United States Patent
Shoji et al.

(10) Patent No.: US 10,865,272 B2
(45) Date of Patent: Dec. 15, 2020

(54) THERMOSETTING RESIN COMPOSITION

(71) Applicant: TEIJIN LIMITED, Osaka (JP)

(72) Inventors: Shinichiro Shoji, Osaka (JP); Kouhei Endo, Osaka (JP); Masaya Shibano, Osaka (JP)

(73) Assignee: TEIJIN LIMITED, Osaka (JP)

( * ) Notice: Subject to any disclaimer, the term of this patent is extended or adjusted under 35 U.S.C. 154(b) by 118 days.

(21) Appl. No.: 16/292,708

(22) Filed: Mar. 5, 2019

(65) Prior Publication Data

US 2019/0194381 A1 Jun. 27, 2019

Related U.S. Application Data

(62) Division of application No. 15/510,457, filed as application No. PCT/JP2015/076205 on Sep. 9, 2015, now abandoned.

(30) Foreign Application Priority Data

| Sep. 11, 2014 | (JP) | 2014-185246 |
| Feb. 20, 2015 | (JP) | 2015-031753 |
| Feb. 25, 2015 | (JP) | 2015-035480 |
| Jul. 30, 2015 | (JP) | 2015-150407 |

(51) Int. Cl.
*C08G 59/40* (2006.01)
*C08G 59/68* (2006.01)
*C08K 5/29* (2006.01)
*C08L 63/00* (2006.01)
*C08G 59/50* (2006.01)
*C07D 491/113* (2006.01)
*C08K 5/18* (2006.01)

(52) U.S. Cl.
CPC ...... *C08G 59/4042* (2013.01); *C07D 491/113* (2013.01); *C08G 59/5033* (2013.01); *C08G 59/686* (2013.01); *C08K 5/18* (2013.01); *C08K 5/29* (2013.01); *C08L 63/00* (2013.01)

(58) Field of Classification Search
CPC ............ C07D 491/113; C08G 59/4042; C08G 59/5033; C08G 59/686; C08K 5/18; C08K 5/29; C08L 63/00
USPC ........................................................ 525/523
See application file for complete search history.

(56) References Cited

U.S. PATENT DOCUMENTS

| 5,079,326 A | 1/1992 | Suzuki et al. |
| 2008/0269428 A1 | 10/2008 | Volle et al. |
| 2011/0224385 A1 | 9/2011 | Shoji et al. |
| 2013/0085273 A1 | 4/2013 | Shoji |
| 2013/0085274 A1 | 4/2013 | Suzuki et al. |
| 2015/0239182 A1 | 8/2015 | Kosaka et al. |

FOREIGN PATENT DOCUMENTS

| JP | 62-1714 A | 1/1987 |
| JP | 2-175756 A | 7/1990 |
| JP | 2001-123043 A | 5/2001 |
| JP | 2006-176549 A | 7/2006 |
| JP | 2008-503628 A | 2/2008 |
| JP | 2010-144121 A | 7/2010 |
| JP | 2010-285557 A | 12/2010 |
| JP | 2011-68814 A | 4/2011 |
| JP | 2012-001476 A | 1/2012 |
| JP | 2012-001478 A | 1/2012 |
| WO | 2010/071213 A1 | 6/2010 |
| WO | 2014/046296 A1 | 3/2014 |

OTHER PUBLICATIONS

Communication dated Mar. 15, 2018, from the Intellectual Property Office of Singapore in counterpart application No. 11201701852V.
International Preliminary Report on Patentability and Written Opinion for International Application No. PCT/JP2015/076205 dated Mar. 23, 2017, 5 pages.
International Search Report of PCT/JP2015/076205 dated Nov. 24, 2015.
Shoji, JP 2010-285557 A machine translation in English Dec. 24, 2010 (Year: 2010); 59 pages.

*Primary Examiner* — David T Karst
(74) *Attorney, Agent, or Firm* — Sughrue Mion, PLLC

(57) ABSTRACT

A thermosetting resin composition which produces no free isocyanate even when a carbodiimide compound is used and provides a cured resin having high heat resistance. The thermosetting resin composition makes it possible to reduce the curing temperature, cures in a short time and provides a cured rein having a high glass transition temperature. The thermosetting resin composition includes:
  (A) an epoxy resin (component A); and
  (B) a cyclic carbodiimide compound (component B) including a cyclic structure having one carbodiimide group in which first nitrogen and second nitrogen are bonded together by a bond group and having 8 to 50 atoms forming the cyclic structure and/or
  (b) a polyvalent amine-based curing agent (component b).

14 Claims, No Drawings

THERMOSETTING RESIN COMPOSITION

CROSS REFERENCE TO RELATED APPLICATIONS

This is a divisional of application Ser. No. 15/510,457 filed Mar. 10, 2017, which is the National Stage of PCT/JP2015/076205 filed Sep. 9, 2015 (which claims priority from Japanese Patent Application Nos. 2014-185246 filed Sep. 11, 2014, 2015-031753 filed Feb. 20, 2015, 2015-035480 filed Feb. 25, 2015, and 2015-150407 filed Jul. 30, 2015), the disclosure of which is incorporated by reference.

TECHNICAL FIELD

The present invention relates to a thermosetting resin composition comprising an epoxy resin and a cyclic carbodiimide. The present invention also relates to a method of using a cyclic carbodiimide as a curing agent or curing accelerator for a thermosetting resin composition.

The present invention also relates to a thermosetting resin composition comprising an epoxy resin and a polyvalent amine-based curing agent and to a cured resin obtained by curing the composition.

BACKGROUND ART

Thermosetting resin compositions are used for a wide range of applications according to the characteristic properties of a resin. Since an epoxy resin in particular is excellent in balance among productivity, cost and reliability as well as electrical insulating properties, it is widely used mainly in electric and electronic fields and automobile and aircraft fields.

Further, to make more effective use of the characteristic properties of the epoxy resin, studies are being made on epoxy resins into which functional groups have been introduced and compositions comprising these. As semiconductor sealing materials and carbon fiber composite materials in particular are having higher performance and becoming more compact, high heat resistance, adhesion to another member and high followability at the time of processing are now required as the characteristic properties of the epoxy resin.

To satisfy these requirements, there is proposed a method of mixing a carbodiimide compound with an epoxy resin (Patent Documents 1 to 5). It is confirmed that adhesion to another member is improved and separation hardly occurs by mixing the carbodiimide compound and that the obtained composition has high flowability and excellent moldability. However, the heat resistance of a cured resin obtained while these characteristic properties are retained is not satisfactory. Although an amine compound, acid anhydride or phenol resin is used as a curing agent for the epoxy resin, when a carbodiimide compound is used in combination, the curing agent reacts with the compound and a free isocyanate derived from the carbodiimide is produced by a high-temperature treatment at the time of curing, thereby causing problems such as limitation to the work environment and the deterioration of another member.

Meanwhile, there is proposed a cyclic carbodiimide compound as a carbodiimide compound which does not produce a free isocyanate (Patent Document 6). Although it is confirmed that the production of a free isocyanate can be suppressed by using the cyclic carbodiimide compound, ample studies are not made on the epoxy resin from the viewpoint of heat resistance.

Meanwhile, it is known that the characteristic properties of a cured resin are greatly influenced by a curing agent used to cure the resin. To make more effective use of the characteristic properties of an epoxy resin, various curing agents are now under study. As a curing agent for the epoxy resin, polyamines, acid anhydrides and imidazoles are used, out of which amine-based curing agents are mainly used as they are various in type and easily selected according to purpose. The amine-based curing agents include aliphatic polyamines, alicyclic polyamines and aromatic polyamines.

By properly selecting one from these amine-based curing agents, the desired mechanical and physical properties of a thermosetting resin composition can be obtained for many purposes.

Along with growing demand for cured resins and the development of peripheral technologies in recent years, high heat resistance, fast curability at the time of heating and curing properties at a relatively low temperature are further required. Especially amine-based curing agents which cure resins at a relatively low temperature and obtain high heat resistance are now under study from the viewpoints of damage to resins and limitation to equipment in use.

In general, the amine-based curing agents have a short pot life. For example, in the case of a mixture of an amine-based curing agent and an epoxy resin described in Patent Document 7, even when it is put in a 10° C. low-temperature environment, a gelation phenomenon occurs in 50 to 70 minutes.

In contrast to this, Patent Document 8 teaches that a thermosetting resin composition having a long pot life is obtained by using an amine-based curing agent containing polyethylene amine. Meanwhile, the polyethylene amine has problems that a high curing temperature of about 200° C. is required, the thermal deterioration of an epoxy resin readily occurs and the cure shrinkage factor at the time of thermal curing becomes large.

As described above, a thermosetting resin composition which has high heat resistance, fast curability at the time of heating, curing properties at a relatively low temperature and a satisfactory pot life from the viewpoint of handling has been desired.

(Patent Document 1) JP-A 62-1714
(Patent Document 2) JP-A 2-175756
(Patent Document 3) JP-A 2001-123043
(Patent Document 4) JP-A 2010-144121
(Patent Document 5) JP-A 2006-176549
(Patent Document 6) JP-A 2010-285557
(Patent Document 7) JP-A 2008-503628
(Patent Document 8) JP-A 2011-068814

DISCLOSURE OF THE INVENTION

It is an object of the present invention to provide a thermosetting resin composition which does not produce a free isocyanate even when a carbodiimide compound is used and provides a cured resin having high heat resistance. The inventors of the present invention conducted intensive studies on a thermosetting resin composition which does not produce a free isocyanate even when a carbodiimide compound is used and provides a cured resin having high heat resistance. As a result, they found that a thermosetting resin composition comprising an epoxy resin and a carbodiimide compound having a specific cyclic structure does not produce a free isocyanate compound at the time of a high-temperature treatment and achieves high heat resistance. Further, they found that a carbodiimide compound having a specific cyclic structure functions effectively as a curing agent or curing accelerator to improve the characteristic properties of a thermosetting resin composition. The present invention was accomplished based on this finding.

It is another object of the present invention to provide a thermosetting resin composition which makes it possible to reduce the curing temperature for the thermosetting resin composition, cures in a short time and provides a cured resin having a high glass transition temperature as well as a cured resin. As a result of intensive studies, they found that a thermosetting resin composition having a low curing temperature and a short curing time is obtained by using a polyvalent amine-based compound having a specific structure out of amine-based curing agents as a curing agent and further that a cured resin obtained by curing this thermosetting resin composition has high heat resistance. The present invention was accomplished based on this finding. That is, an object of the present invention is attained by the following inventions.

1. A thermosetting resin composition comprising:
(A) an epoxy resin (component A); and
(B) a cyclic carbodiimide compound (component B) including a cyclic structure having one carbodiimide group and represented by the following formula (B-i) in which first nitrogen and second nitrogen are bonded together by a bond group and having 8 to 50 atoms forming the cyclic structure:

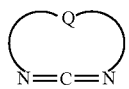

(B-i)

(wherein Q is bivalent to tetravalent bond group which is an aliphatic group, alicyclic group, aromatic group or a combination of these groups, and may contain a hetero atom or substituent); and/or
(b) a polyvalent amine-based curing agent (component b) represented by the following formula (b-i):

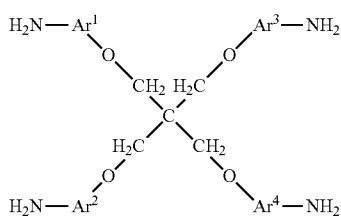

(b-i)

(wherein $Ar^1$ to $Ar^4$ are each independently a phenylene group or naphthalene-diyl group which may be substituted by a substituent).

<Mode Comprising Cyclic Carbodiimide Compound (Component B)>

The invention comprising a cyclic carbodiimide compound (component B) has the following modes 2 to 11.

2. The thermosetting resin composition in the above paragraph 1, comprising:
(A) an epoxy resin (component A); and
(B) a cyclic carbodiimide compound (component B) including a cyclic structure having one carbodiimide group and represented by the following formula (B-i) in which first nitrogen and second nitrogen are bonded together by a bond group and having 8 to 50 atoms forming the cyclic structure:

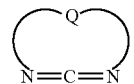

(B-i)

(wherein Q is bivalent to tetravalent bond group which is an aliphatic group, alicyclic group, aromatic group or a combination of these groups, and may contain a hetero atom or substituent).

3. The thermosetting resin composition in the above paragraph 2, wherein the component B is a polyvalent cyclic carbodiimide compound having at least two carbodiimide groups in one molecule.

4. The thermosetting resin composition in the above paragraph 2, wherein the component B is a compound represented by the following formula (B-ii):

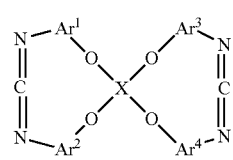

(B-ii)

(wherein X is a tetravalent group represented by the following formula (B-iii). $Ar^1$ to $Ar^4$ are each independently an orthophenylene group or 1,2-naphthalene-diyl group which may be substituted by an alkyl group having 1 to 6 carbon atoms or phenyl group).

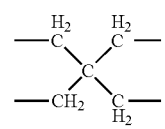

(B-iii)

5. The thermosetting resin composition in the above paragraph 2, wherein the content of the cyclic carbodiimide compound (component B) is 0.01 to 50 parts by weight based on 100 parts by weight of the epoxy resin (component A).

6. The thermosetting resin composition in the above paragraph 2, wherein the glass transition temperature of a cured resin is 2° C. or more higher than the glass transition temperature of a cured resin obtained by curing a thermosetting resin composition comprising no component B under the same conditions.

7. The thermosetting resin composition in the above paragraph 2, further comprising a curing agent (component C).

8. The thermosetting resin composition in the above paragraph 2, further comprising a curing accelerator (component D).

9. A process for producing a cured resin, comprising the step of heating the thermosetting resin composition in the above paragraph 1.

10. A method of using a cyclic carbodiimide compound (component B) including a cyclic structure having one carbodiimide group and represented by the following formula (B-i) in which first nitrogen and second nitrogen are bonded together by a bond group and having 8 to 50 atoms forming the cyclic structure as a curing agent for an epoxy resin (component A):

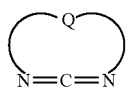

(wherein Q is bivalent to tetravalent bond group which is an aliphatic group, alicyclic group, aromatic group or a combination of these groups, and may contain a hetero atom or substituent).

11. A method of using a cyclic carbodiimide compound (component B) including a cyclic structure having one carbodiimide group and represented by the following formula (B-i) in which first nitrogen and second nitrogen are bonded together by a bond group and having 8 to 50 atoms forming the cyclic structure as a curing accelerator for an epoxy resin (component A):

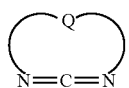

(wherein Q is bivalent to tetravalent bond group which is an aliphatic group, alicyclic group, aromatic group or a combination of these groups, and may contain a hetero atom or substituent).

<Mode Comprising Polyvalent Amine-Based Curing Agent (Component b)>

The invention comprising a polyvalent amine-based curing agent (component b) has the following modes 12 to 21.

12. The thermosetting resin composition in the above paragraph 1, comprising:
(A) an epoxy resin (component A); and
(b) a polyvalent amine-based curing agent (component b) represented by the following formula (b-i):

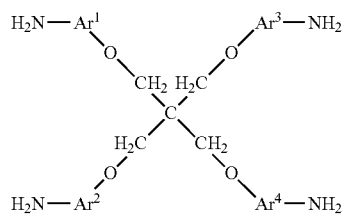

(wherein $Ar^1$ to $Ar^4$ are each independently a phenylene group or naphthalene-diyl group which may be substituted by a substituent).

13. The thermosetting resin composition in the above paragraph 12, comprising 10 to 50 parts by weight of the polyvalent amine-based curing agent (component b) based on 100 parts by weight of the epoxy resin (component A).

14. The thermosetting resin composition in the above paragraph 12, comprising 10 to 45 parts by weight of the polyvalent amine-based curing agent (component b) based on 100 parts by weight of the epoxy resin (component A).

15. The thermosetting resin composition in the above paragraph 12, wherein the difference between the glass transition temperature (Tg·2H) of a cured resin after 2 hours of curing and the glass transition temperature (Tg·4H) of a cured resin after 4 hours of curing is less than 10° C. at a thermal curing temperature of 160° C. to 200° C.

16. The thermosetting resin composition in the above paragraph 12, wherein the glass transition temperature (Tg·160° C./4H) of a cured resin obtained after 4 hours of curing at a thermal curing temperature of 160° C. is 175° C. or higher.

17. The thermosetting resin composition in the above paragraph 12, wherein the glass transition temperature (Tg·180° C./2H) of a cured resin obtained after 2 hours of curing at a thermal curing temperature of 180° C. is 175° C. or higher.

18. The thermosetting resin composition in the above paragraph 12, wherein the epoxy resin (component A) is a bisphenol type epoxy resin.

19. A cured resin comprising a compound represented by the following formula (b-ii):

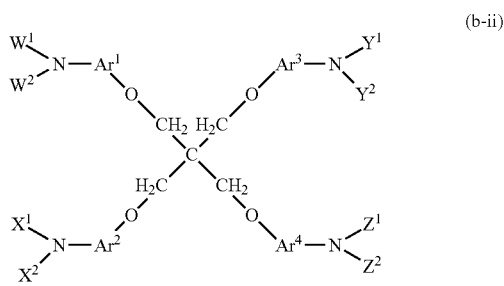

(wherein $Ar^1$ to $Ar^4$ are each independently a phenylene group or naphthalene-diyl group which may be substituted by a substituent. $W^1$, $W^2$, $X^1$, $X^2$, $Y^1$, $Y^2$, $Z^1$ and $Z^2$ are each independently selected from a hydrogen atom and group represented by the following formula (b-iii), with the proviso that at least two out of $W^1$, $W^2$, $X^1$, $X^2$, $Y^1$, $Y^2$, $Z^1$ and $Z^2$ are groups represented by the following formula (b-iii))

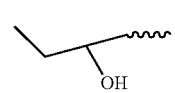

(wherein the wavy part represents an epoxy resin residue).

20. The cured resin in the above paragraph 19, wherein the content of the compound represented by the formula (b-ii) is not less than 50 wt % based on the total weight.

21. The cured resin in the above paragraph 19 which is obtained by curing a thermosetting resin composition comprising (A) an epoxy resin (component A) and (b) a polyvalent amine-based curing agent (component b) represented by the following formula (b-i):

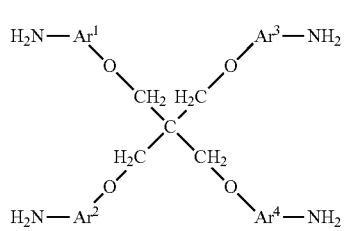

(wherein $Ar^1$ to $Ar^4$ are each independently a phenylene group or naphthalene-diyl group which may be substituted by a substituent).

<Mode Comprising Both Cyclic Carbodiimide Compound (Component B) and Polyvalent Amine-Based Curing Agent (Component b)>

The present invention includes a thermosetting resin composition comprising an epoxy resin (component A), a cyclic carbodiimide compound (component B) and a polyvalent amine-based curing agent (component b) and a cured resin thereof.

BEST MODE FOR CARRYING OUT THE INVENTION

The present invention will be described in detail hereinunder. The thermosetting resin composition of the present invention comprises an epoxy resin (component A) and a cyclic carbodiimide compound (component B) and/or a polyvalent amine-based curing agent (component b). That is, the thermosetting resin composition of the present invention comprises an epoxy resin (component A) and at least one selected from the group consisting of a cyclic carbodiimide compound (component B) and a polyvalent amine-based curing agent (component b). The present invention includes (1) a mode comprising an epoxy resin (component A) and a cyclic carbodiimide compound (component B), (2) a mode comprising an epoxy resin (component A) and a polyvalent amine-based curing agent (component b) and (3) a mode comprising an epoxy resin (component A), a cyclic carbodiimide compound (component B) and a polyvalent amine-based curing agent (component b).

<Mode Comprising Cyclic Carbodiimide Compound (Component B)>

<Epoxy Resin (Component A)>

In the present invention, the epoxy resin (component A) is a monomer, oligomer or polymer having at least two epoxy groups in one molecule. Examples thereof include hydroquinone type epoxy resins, bisphenol A type epoxy resins, bisphenol F type epoxy resins, biphenyl type epoxy resins, stilbene type epoxy resins, phenol novolak type epoxy resins, cresol novolak type epoxy resins, naphthol novolak type epoxy resins, triphenol methane type epoxy resins, alkyl modified triphenol methane type epoxy resins, dicyclopentadiene modified phenol type epoxy resins, phenol aralkyl type epoxy resins (having a phenylene skeleton or biphenylene skeleton), naphthol aralkyl type epoxy resins (having a phenylene skeleton or biphenylene skeleton), terpene modified phenol type epoxy resins, triazine nucleus-containing epoxy resins, alicyclic epoxy resins and condensate ring aromatic hydrocarbon modified epoxy resins. The present invention is not limited to these. These epoxy resins may be used alone or in combination of two or more.

<Cyclic Carbodiimide Compound (Component B)>

The cyclic carbodiimide compound (component B) includes a cyclic structure represented by the following formula (B-i).

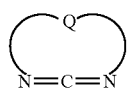

(B-i)

In the above formula, Q is bivalent to tetravalent bond group which is an aliphatic group, alicyclic group, aromatic group or a combination of these groups, and may contain a hetero atom or substituent.

In the above formula, Q is preferably a group represented by —$Ar^a$—O—X—O—$Ar^b$—. $Ar^a$ and $Ar^b$ are each independently a phenylene group or naphthalene-diyl group which may be substituted by an alkyl group having 1 to 6 carbon atoms or phenyl group. X is preferably an alkanediyl group when the cyclic carbodiimide compound has two cyclic structures. When the cyclic carbodiimide compound has four cyclic structures, X is preferably an alkanetetrayl group.

In the present invention, the cyclic carbodiimide compound (component B) has only one carbodiimide group in one cyclic structure. The component B may have a plurality of cyclic structures.

The cyclic carbodiimide compound (component B) has 8 to 50 atoms in the cyclic structure. The number of atoms in the cyclic structure means the number of atoms constituting the cyclic structure directly. For example, when the cyclic structure is an 8-membered ring, the number of atoms is 8 and when the cyclic structure is a 50-membered ring, the number of atoms is 50. When the number of atoms in the cyclic structure is smaller than 8, the stability of the cyclic carbodiimide compound lowers, whereby it may be difficult to store and use the cyclic carbodiimide compound. Although there is no limitation to the upper limit number of members of the ring from the viewpoint of reactivity, it is difficult to synthesize a cyclic carbodiimide compound having a cyclic structure with more than 50 atoms, which may cause a big increase in cost or the deterioration of the physical properties of the thermosetting resin composition. From this point of view, the number of atoms in the cyclic structure is preferably 10 to 30, more preferably 10 to 20. Examples of the cyclic carbodiimide compound include compounds described in WO2010/071213.

The cyclic carbodiimide compound (component B) is preferably a polyvalent cyclic carbodiimide compound having at least two carbodiimide groups in one molecule in order to improve the heat resistance of a cured resin. Especially when the cyclic carbodiimide compound is used as a curing agent for the thermosetting resin composition, it preferably contains two or three carbodiimide groups in one molecule from the viewpoint of curing performance. These cyclic carbodiimide compounds may be used in combination of two or more.

From the viewpoint of compatibility with another component constituting the thermosetting resin composition, the molecular weight of the cyclic carbodiimide compound (component B) is preferably 100 to 1,000. When the molecular weight is lower than 100, the cyclic carbodiimide compound vaporizes at the time of thermal curing and may not function. When the molecular weight is higher than 1,000, the cyclic carbodiimide compound is rarely compatible with another component constituting the thermosetting resin composition and may not obtain satisfactory curing properties. From this point of view, the molecular weight of the cyclic carbodiimide compound (component B) is more preferably 100 to 750, much more preferably 250 to 750.

A compound represented by the following formula (B-ii) is given as an example of the cyclic carbodiimide compound (component B).

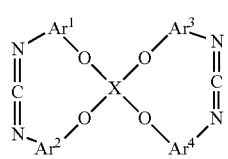

(B-ii)

In the above formula, X is a tetravalent group represented by the following formula (B-iii). In the above formula, $Ar^1$ to $Ar^4$ are each independently an orthophenylene group or 1,2-naphthalene-diyl group which may be substituted by a substituent. Examples of the substituent include alkyl groups having 1 to 20 carbon atoms, aryl group having 6 to 15 carbon atoms, halogen atom, nitro group, amide group, hydroxyl group, ester group, ether group and aldehyde group. These aromatic groups may have a heterocyclic structure containing a hetero atom. Examples of the hetero atom include O, N, S and P.

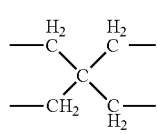

(B-iii)

A compound represented by the following formula (B-iv) is given as a preferred example of the cyclic carbodiimide compound.

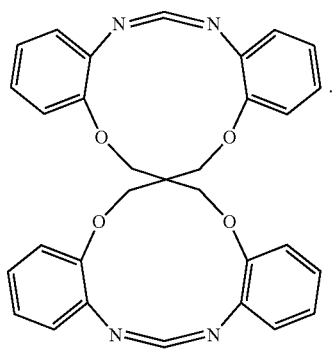

(B-iv)

These cyclic carbodiimide compounds (component B) may be produced by known processes disclosed in documents and patent publications (for example, a process disclosed in WO2010/071213).

The content of the cyclic carbodiimide compound (component B) is preferably 0.01 to 50 parts by weight, more preferably 0.05 to 30 parts by weight, much more preferably 0.1 to 20 parts by weight, most preferably 1 to 20 parts by weight based on 100 parts by weight of the epoxy resin (component A). When the content is lower than 0.01 part by weight, the effect obtained by addition may not be obtained. When the content is higher than 50 parts by weight, there may occur problems with compatibility with the epoxy resin (component A) and bleed-out.

The thermosetting resin composition of the present invention comprises the epoxy resin (component A) and the cyclic carbodiimide compound (component B) as essential components. The component B may be used as a curing agent, curing accelerator or hydrolysis inhibitor for the epoxy resin and a cured resin thereof.

When the cyclic carbodiimide compound (component B) is used as a curing agent, the content of the cyclic carbodiimide compound (component B) is preferably 0.01 to 2 equivalents, more preferably 0.02 to 1.0 equivalent, much more preferably 0.05 to 0.8 equivalent based on the epoxy group of the epoxy resin (component A).

When the cyclic carbodiimide compound (component B) is used as a curing accelerator, the content of the cyclic carbodiimide compound (component B) is preferably 0.01 to 30 parts by weight based on 100 parts by weight of the epoxy resin (component A). Since the cyclic carbodiimide compound (component B) is relatively stable in the thermosetting resin composition at an ordinary temperature of 25° C., even when a large amount of the cyclic carbodiimide compound is contained, curing proceeds and handling does not become worse. Therefore, even when the content is higher than 5 parts by weight, the cyclic carbodiimide compound functions effectively as a curing accelerator. When the content is lower than 0.01 part by weight, an acceleration effect may not be obtained. When the content is higher than 30 parts by weight, the cyclic carbodiimide compound may inhibit a reaction between the epoxy resin and the curing agent. From this point of view, the content of the cyclic carbodiimide compound is more preferably 0.05 to 25 parts by weight, much more preferably 0.1 to 20 parts by weight.

<Curing Agent (Component C)>

The thermosetting resin composition of the present invention may comprise a curing agent (component C) in addition to the cyclic carbodiimide (component B). In this case, when a curing accelerator (component D) which will be described hereinafter is contained in the epoxy resin, as the cyclic carbodiimide (component B) serves as a curing agent, two or more curing agents are existent. When the curing accelerator (component D) which will be described hereinafter is not contained in the thermoplastic resin, as the cyclic carbodiimide compound (component B) serves as a curing accelerator, only the curing agent (component C) is contained as a curing agent in this case.

A known curing agent for epoxy resins may be generally used as the curing agent (component C). The curing agent is a polyamine (alicyclic polyamine, aromatic polyamine or modified polyamine), acid anhydride, polyphenol or polymercaptan. Specific examples of the curing agent include ethylene triamine, triethylene tetramine, tetraethylene pentamine, triethylene diamine, isophorone diamine, N-aminoethyl piperazine, 3,9-bis(3-aminopropyl)-2,4,8,10-tetraoxyspiro-(5,5')-undecane adduct, dicyane diamide, diaminodiphenyl sulfone, phenylene diamine, xylylene diamine, 4,4'-diamino-3,3'-diethyl diphenyl methane, 4,4'-diaminodicyclohexyl methane, diethyl toluene diamine, phthalic anhydride, tetrahydrophthalic anhydride, methyl nadic anhydride, pyromellitic anhydride, phenol novolak, cresol novolak, phenol aralkyl, naphthol aralkyl, liquid phenol resin, polymercaptan and 2-ethyl-4-methyl imidazole. These curing agents may be used alone or in combination of two or more.

The content of the curing agent (component C) differs according to whether the cyclic carbodiimide compound (component B) functions as a curing agent or curing accelerator. When the cyclic carbodiimide compound (component B) functions as a curing agent, the content of the cyclic carbodiimide compound (component B) is preferably less than 50 wt % based on the total amount of the cyclic carbodiimide compound (component B) and the curing agent (component C). When the curing agent (component C) is used in combination, to provide the characteristic feature of the component C, the content of the component C is preferably not less than 50 wt %.

The component C may be contained to ensure that the total content of the carbodiimide group of the cyclic carbodiimide compound (component B) and the reaction group (acid anhydride, amino group or phenol group) of the curing agent (component C) is 0.1 to 5 equivalents based on the epoxy group of the epoxy resin (component A). Since curing performance becomes excellent when the content of the reaction group becomes 1 equivalent based on the epoxy group though it differs according to the type of the curing agent, the above total content is preferably 0.3 to 3 equivalents, more preferably 0.5 to 2 equivalents.

The reaction group refers to a group able to react with an epoxy group. When one group can react with two epoxy groups, the group is counted as two reaction groups. For example, since an amino group (—$NH_2$) can react with two epoxy groups, it is counted as two reaction groups.

In the present invention, even when the cyclic carbodiimide compound (component B) is used as a curing agent, the content of the other curing agent (component C) is preferably adjusted to ensure that the content of the reaction group of the curing agent (component C) becomes 1 equivalent based on the epoxy group of the epoxy resin (component A). Since the cyclic carbodiimide compound (component B) reacts with a hydroxyl group, amino group, phenol group or decomposed product of an acid anhydride besides the epoxy group of the epoxy resin (component A), additional curing can be expected as compared with a thermosetting resin composition comprising no cyclic carbodiimide compound (component B). The content of the cyclic carbodiimide compound (component B) is preferably 0.01 to 2 equivalents, more preferably 0.02 to 1 equivalent, much more preferably 0.05 to 0.8 equivalent based on the epoxy group as described above.

<Curing Accelerator (Component D)>

The thermosetting resin composition of the present invention may comprise a curing accelerator (component D) in addition to the cyclic carbodiimide (component B). As described above, the cyclic carbodiimide compound (component B) functions as a curing agent for the thermosetting resin.

A known curing accelerator for epoxy resins may be generally used as the curing accelerator (component D).

Examples of the curing accelerator include imidazoles such as 2-ethyl-4-methylmidazole and 1-methylimidazole; tertiary amines such as benzyl dimethylamine and N,N-dimethylaniline, quaternary ammonium salts such as tetramethylammonium chloride and benzyl triethylammonium chloride; organic phosphine compounds such as alkyl phosphine, phenyl phosphine, dialkyl phosphine, diphenyl phosphine, trialkyl phosphine and triphenyl phosphine; phosphonium salts such as tetra-n-butyl phosphonium, o,o-diethylphosphorodithionate, tetrabutyl phosphonium and benzotriazolate; and metal salts such as zinc octylate and zinc stearate, and metal complexes such as zinc acetyl acetone and zinc benzoyl acetone.

The content of the curing accelerator (component D) is preferably 0.01 to 5 parts by weight based on 100 parts by weight of the total of the epoxy resin (component A), the cyclic carbodiimide compound (component B) and the curing agent (component C) when it is used. When the content of the curing accelerator (component D) is lower than 0.01 part by weight, an acceleration effect may not be obtained. When the content is higher than 5 parts by weight, curing is accelerated, whereby handling may become worse at the time of curing the thermosetting resin composition. From this point of view, the content is more preferably 0.05 to 3 parts by weight, much more preferably 0.1 to 1.5 parts by weight.

<Other Components>

The thermosetting resin composition of the present invention may comprise additives including an inorganic filler; coupling agent such as silane coupling agent, titanate coupling agent, aluminum coupling agent or aluminum/zirconium coupling agent; flame retardant such as brominated epoxy resin, antimony oxide or phosphorus compound; inorganic ion exchanger such as bismuth oxide hydrate; coloring agent such as carbon black or red oxide; silicone oil; silicone-based or rubber-based stress reducing agent; release agent such as natural wax, synthetic wax, higher fatty acid, metal salt thereof or paraffin; and antioxidant as required as long as they are not adverse to the object of the present invention in addition to the epoxy resin (component A), the cyclic carbodiimide compound (component B), the curing agent (component C) and the curing accelerator (component D).

The thermosetting resin composition of the present invention may be advantageously used for applications in which heat resistance is required, for example, semiconductor sealing materials, prepregs and other composite matrix materials, printed circuit boards, laminate sheets, electrical insulating materials and pastes.

<Process for Producing Thermosetting Resin Composition>

The thermosetting resin composition of the present invention may be produced by a known process. For example, the resin composition can be prepared by mixing together the epoxy resin (component A), the cyclic carbodiimide compound (component B), the curing agent (component C), the curing accelerator (component D) and other additives by means of a mixer. The mixing method is not particularly limited and a conventionally known method may be used. A solution state or molten state is preferred from the viewpoint of homogeneity.

After mixing, the mixture is kneaded under heating by means of a kneading machine such as a roll, kneader or extruder, cooled and pulverized to obtain a resin composition as a solid component.

To prepare the resin composition as a solution, various solvents may be used but a solvent which is inactive to the epoxy resin, the cyclic carbodiimide compound, the curing agent, the curing accelerator and other additives and dissolves some or all of these components may be advantageously used. Examples of the solvent include hydrocarbon-based solvents, ketone-based solvents, ester-based solvents, ether-based solvents, halogen-based solvents and amide-based solvents.

The thermosetting resin composition of the present invention is preferably prepared by dissolving the cyclic carbodiimide compound (component B) in the epoxy resin (component A) in advance and mixing the curing agent (component C), the curing accelerator (component D) and other additives with the resulting solution. The homogeneity of the cyclic carbodiimide compound (component B) in the resin composition is improved and the characteristic properties of the cured resin may become better by dissolving the cyclic carbodiimide compound (component B) in the epoxy resin (component A) in advance. The characteristic properties of the cured resin include heat resistance.

The method of dissolving the cyclic carbodiimide compound (component B) in the epoxy resin (component A) in advance is not particularly limited and a conventionally known method may be used. For example, a method in which the cyclic carbodiimide compound is heated to be dissolved in the epoxy resin or a method in which the cyclic carbodiimide compound is dissolved in a solvent may be employed.

When the cyclic carbodiimide compound is heated to be dissolved, a kneading machine such as a roll, kneader or extruder may be used to heat and knead it. The kneaded product is pulverized after cooling to obtain a solid component. The heating temperature is preferably 25 to 200° C. When the heating temperature is lower than 25° C., dissolution may become difficult. When the heating temperature is higher than 200° C., the epoxy group of the epoxy resin (component A) and the carbodiimide group of the cyclic carbodiimide compound (component B) react with each other excessively to increase the melt viscosity, whereby handling may become difficult.

When the cyclic carbodiimide compound is dissolved in a solvent, a solvent which is inactive to the epoxy resin and the cyclic carbodiimide compound and dissolves some or all of the components may be advantageously used. As the solvent, a hydrocarbon-based solvent, ketone-based solvent, ester-based solvent, ether-based solvent, halogen-based solvent or amide-based solvent may be used. After dissolution, the solvent is removed to obtain a solid or liquid component.

The thermosetting resin composition of the present invention may be processed by a generally known method according to each purpose. Processing is not particularly limited but includes molding, coating and impregnation.

To manufacture a semiconductor device by using the thermosetting resin composition of the present invention to seal an electronic part such as a semiconductor element, the thermosetting resin composition should be cured and molded by a molding method such as transfer molding, compression molding or injection molding.

To manufacture a prepreg, the thermosetting resin composition of the present invention should be impregnated as resin varnish into a base material. The resin varnish is a mixture of the epoxy resin, the cyclic carbodiimide compound, the curing agent, the curing accelerator and other additives or a solution prepared by dissolving these in a solvent. As the base material, an organic fiber such as glass cloth, carbon fiber or aramid may be used.

Further, to manufacture metal foil with a resin, a method in which the thermosetting resin composition of the present invention as resin varnish is applied to metal foil by a known method, such as methods with a comma coater, knife coater or curtain coater and a volatile component such as a solvent is dried and removed to form a resin layer by half curing the thermosetting resin composition of the present invention may be employed.

<Thermal Curing Method>

To thermally cure the thermosetting resin composition of the present invention, a known method may be generally used. Basically, by heating at a curing temperature suitable for the epoxy resin and the curing agent in use, the thermosetting resin composition of the present invention can achieve a satisfactory cure degree.

Further, when the cyclic carbodiimide compound is used as a curing agent or curing accelerator, as compared with a thermosetting resin composition comprising no cyclic carbodiimide compound, satisfactory curing performance may be obtained in a short time or at a low temperature, whereby the suppression of the thermal deterioration of components such as the epoxy resin by a long-term treatment or high-temperature treatment can be expected.

The curing temperature which greatly differs according to the epoxy resin and the curing agent in use is preferably selected from a range from 25° C. to 250° C. When the curing temperature is lower than 25° C., the thermosetting resin composition may not cure completely. When the curing temperature is higher than 250° C., curing proceeds but the resin composition itself deteriorates by heat and satisfactory curing performance may not be obtained. From this point of view, the curing temperature is more preferably 25 to 200° C.

<Method of Using Cyclic Carbodiimide Compound (Component B) as Curing Agent>

The present invention includes a method of using a cyclic carbodiimide compound (component B) including a cyclic structure having one carbodiimide group and represented by the formula (B-i) in which first nitrogen and second nitrogen are bonded together by a bond group and having 8 to 50 atoms forming the cyclic structure as a curing accelerator for the epoxy resin (component A).

The cyclic carbodiimide compound (component B) is used as a curing agent for the epoxy resin (component A). When the cyclic carbodiimide compound (component B) is used as a curing agent, it is preferably used in combination with the other curing agent (component C) and the curing accelerator (component D). The reason that it is used in combination with the other curing agent is that the carbodiimide group of the cyclic carbodiimide compound acts effectively on the epoxy group or hydroxyl group of the epoxy resin and the acid anhydride, amino group or phenol group of the other curing agent, thereby developing curing performance and durability after curing.

<Method of Using Cyclic Carbodiimide Compound (Component B) as Curing Accelerator>

The present invention includes a method of using the cyclic carbodiimide compound (component B) including a cyclic structure having one carbodiimide group and represented by the formula (B-i) in which first nitrogen and second nitrogen are bonded together by a bond group and having 8 to 50 atoms forming the cyclic structure as a curing accelerator for the epoxy resin (component A).

When the cyclic carbodiimide compound (component B) is used as a curing accelerator, the above-described generally known epoxy resins (component A) and curing agents (component C) may be used. The epoxy resins and the curing agents may be used alone or in combination of two or more, respectively. As the epoxy resin, biphenol type epoxy resins, phenol novolak type epoxy resins, cresol novolak type epoxy resins and naphthol novolak type epoxy resins may be advantageously used. As the curing agent, phenol novolak may be advantageously used.

Since the cyclic carbodiimide compound is relatively stable in the thermosetting resin composition at an ordinary temperature of 25° C., even when a large amount of the cyclic carbodiimide compound is contained, curing proceeds and handling does not become worse. Therefore, even when the content of the cyclic carbodiimide compound is higher than 5 parts by weight, the cyclic carbodiimide compound functions effectively as a curing accelerator. When the content is lower than 0.01 part by weight, an acceleration effect may not be obtained. When the content is higher than 30 parts by weight, the cyclic carbodiimide compound may inhibit a reaction between the epoxy resin and the curing agent. From this point of view, the content is more preferably 0.05 to 25 parts by weight, much more preferably 0.1 to 20 parts by weight.

The feature obtained when the cyclic carbodiimide compound is used as a curing accelerator is that the cyclic carbodiimide compound improves the heat resistance of the thermosetting resin composition, depending on the content thereof. This is because the cyclic carbodiimide compound promotes crosslinking between the epoxy resin and the curing agent and also contributes to the crosslinking to improve the cure degree in the above process. Therefore, a thermosetting resin composition having any high level of heat resistance can be prepared by controlling the content of the cyclic carbodiimide compound.

<Cured Resin>

The cured resin obtained by thermally curing the thermosetting resin composition of the present invention has a glass transition temperature which is 2° C. or more higher than the glass transition temperature of a cured resin obtained by curing a thermosetting resin composition comprising no cyclic carbodiimide compound (component B) under the same conditions.

This is because the cyclic carbodiimide compound (component B) which is contained as a curing agent or curing accelerator contributes to crosslinking to improve the cure degree of the cured resin as described above. In application fields in which the resin composition of the present invention is used, high heat resistance is important. Therefore, the glass transition temperature of the cured resin is preferably 4° C. or more higher, more preferably 6° C. or more higher, most preferably 8° C. or more higher than the glass transition temperature of the above cured resin. From this point of view, it is preferred that the amounts of the cyclic carbodiimide compound, the other curing agent and the curing accelerator to be added to the epoxy resin of the resin composition should be optimized.

Although the glass transition temperature of the cured resin can be raised by adding the cyclic carbodiimide compound (component B), this effect can be further enhanced with a combination of the epoxy resin (component A) and the curing agent (component C). This is due to the fact that the function mechanism of the cyclic carbodiimide (component B) differs according to a combination of the epoxy resin (component A) and the curing agent (component C). Preferred examples of the combination of the epoxy resin (component A) and the curing agent (component C) include a combination of a bisphenol type epoxy resin and an amine-based curing agent, a combination of a bisphenol type epoxy resin and a liquid phenol resin, a combination of a cresol novolak type epoxy resin and phenol novolak, a combination of a biphenyl type epoxy resin and phenol novolak, a combination of a dicyclopentadiene modified phenol type epoxy resin and phenol novolak, and a combination of a polyfunctional epoxy resin having 3 or more epoxy groups and phenol novolak. The number of the epoxy resins (component A) and the number of the curing agents (component C) to be combined may be two or more, respectively.

<Mode Comprising Polyvalent Amine-Based Curing Agent (Component b)>
<Polyvalent Amine-Based Curing Agent (Component b)>

The polyvalent amine-based curing agent (component b) used in the present invention is represented by the following formula (b-i)

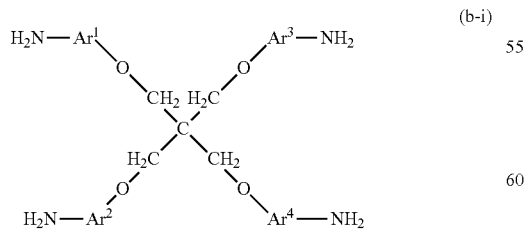

(b-i)

In the above formula, $Ar^1$ to $Ar^4$ are each independently a phenylene group or naphthalene-diyl group which may be substituted by a substituent. The substituent is an aliphatic group having 1 to 20 carbon atoms, alicyclic group having 3 to 20 carbon atoms, aromatic group having 5 to 15 carbon atoms, halogen atom, nitro group, amide group, hydroxyl group, ester group, ether group, aldehyde group or a combination thereof.

An alkyl group having 1 to 20 carbon atoms is given as an example of the aliphatic group. Examples of the alkyl group having 1 to 20 carbon atoms include methyl group, ethyl group, propyl group, butyl group, pentyl group, hexyl group, heptyl group, octyl group, nonyl group, decyl group, dodecyl group and hexadecyl group.

A cycloalkyl group having 3 to 20 carbon atoms is given as an example of the alicyclic group. Examples of the cycloalkyl group having 3 to 20 carbon atoms include cyclopropyl group, cyclobutyl group, cyclopentyl group, cyclohexyl group, cycloheptyl group, cyclooctyl group, cyclononyl group, cyclodecyl group, cyclododecyl group and cyclohexadecyl group.

An aryl group having 5 to 15 carbon atoms, which may have a heterocyclic structure containing a hetero atom, is given as an example of the aromatic group. Examples of the aryl group having 5 to 15 carbon atoms include phenyl group and naphthyl group.

The following compounds are given as examples of the polyvalent amine-based curing agent (component b).

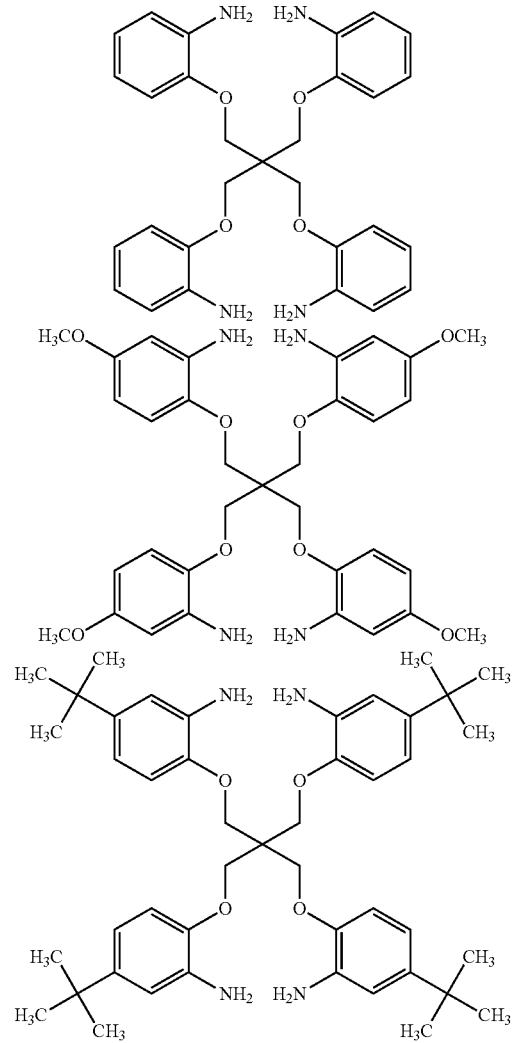

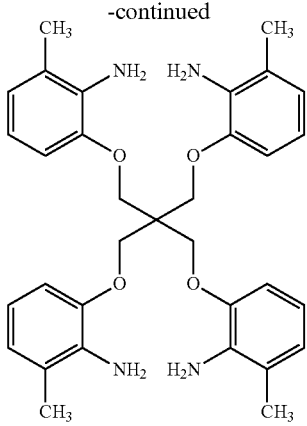

These polyvalent amine-based curing agents (component b) may be produced by known methods described in documents and patent publications (for example, a method described in U.S. Pat. No. 5,645,494).

<Epoxy Resin (Component A)>

The epoxy resin (component A) is a monomer, oligomer or polymer having at least two epoxy groups in one molecule. Examples of the epoxy resin include hydroquinone type epoxy resins, bisphenol A type epoxy resins, bisphenol F type epoxy resins, biphenyl type epoxy resins, stilbene type epoxy resins, phenol novolak type epoxy resins, cresol novolak type epoxy resins, naphthol novolak type epoxy resins, triphenol methane type epoxy resins, alkyl modified triphenol methane type epoxy resins, dicyclopentadiene modified phenol type epoxy resins, phenol aralkyl type epoxy resins (having a phenylene skeleton or biphenylene skeleton), naphthol aralkyl type epoxy resins (having a phenylene skeleton or biphenylene skeleton), terpene modified phenol type epoxy resins, triazine nucleus-containing epoxy resins, alicyclic epoxy resins and condensate ring aromatic hydrocarbon modified epoxy resins. The present invention is not limited to these. These epoxy resins may be used alone or in combination of two or more.

Bisphenol type epoxy resins are preferred as they enable a filler to be highly filled due to a reduction in density at the time of melting and from the viewpoint of adhesion to graphite as a filler. From the above point of view, the epoxy resin is more preferably a bisphenol type epoxy resin having a number average molecular weight of 500 to 5,000, much more preferably a bisphenol type epoxy resin having a number average molecular weight of 800 to 2,000.

Especially, work efficiency at the time of producing the cured resin and moldability at the time of thermal curing become high by selecting an epoxy resin (component A) having a number average molecular weight within this range. When the number average molecular weight of the bisphenol type epoxy resin is lower than 500, the resin become liquid, thereby reducing work efficiency at the time of producing a molding material. When the number average molecular weight of the bisphenol type epoxy resin is higher than 5,000, the melt viscosity of the resin becomes high, whereby a problem with moldability may occur. The number average molecular weight of the epoxy resin is measured with a gel permeation chromatograph by dissolving the resin in tetrahydrofuran and using polystyrene as a reference material.

<Thermosetting Resin Composition>

The thermosetting resin composition of the present invention comprises the epoxy resin (component A) and the polyvalent amine-based curing agent (component b) as essential components.

The content of the polyvalent amine-based curing agent (component b) is preferably 10 to 50 parts by weight based on 100 parts by weight of the epoxy resin (component A). To improve the curing performance of the resin composition, the equivalent of the epoxy group of the epoxy resin (component A) is preferably close to the equivalent of the amino group of the polyvalent amine-based curing agent (component b). This is because the crosslink density is improved by an efficient reaction between the epoxy group and the amino group. When the content of the polyvalent amine-based curing agent (component b) is lower than 10 parts by weight based on 100 parts by weight of the epoxy resin (component A), the crosslink density does not rise and the glass transition temperature Tg may become low. When the content of the polyvalent amine-based curing agent (component b) is higher than 50 parts by weight based on 100 parts by weight of the epoxy resin (component A), the crosslink density does not rise and the glass transition temperature Tg may become low as well. Therefore, to improve the curing performance of the thermosetting resin composition, the content of the polyvalent amine-based curing agent (component b) is more preferably 12 to 48 parts by weight, much more preferably 15 to 45 parts by weight based on 100 parts by weight of the epoxy resin (component A).

The thermosetting resin composition of the present invention may comprise the other curing agent and the curing accelerator as long as they are not adverse to the purpose of using the polyvalent amine-based curing agent (component b).

Known curing agents for epoxy resins may be generally used as the other curing agent and include polyamines (alicyclic polyamines, aromatic polyamines, modified polyamines), acid anhydrides, polyphenols, polymercaptans and cyclic carbodiimide compounds.

Specific examples of the curing agent include ethylene triamine, triethylene tetramine, tetraethylene pentamine, triethylene diamine, isophorone diamine, N-aminoethyl piperazine, 3,9-bis(3-aminopropyl)-2,4,8,10-tetraoxyspiro-(5,5')-undecane adduct, dicyane diamide, diaminodiphenyl sulfone, phenylene diamine, xylylene diamine, 4,4'-diamino-3,3'-diethyl diphenyl methane, 4,4'-diaminodicyclohexyl methane, diethyl toluene diamine, phthalic anhydride, tetrahydrophthalic anhydride, methylnadic anhydride, pyromellitic anhydride, phenol novolak, cresol novolak, phenol aralkyl, naphthol aralkyl, liquid phenol resin, polymercaptan, 2-ethyl-4-methyl imidazole and cyclic carbodiimide compounds described in JP-A 2010-285557. These curing agents may be used alone or in combination of two or more.

The content of the other curing agent is not particularly limited but preferably such that the total content of the amino group of the polyvalent amine-based curing agent (component b) and the reaction group (such as acid anhydride, amino group or phenol group) of the other curing agent becomes 0.1 to 5 equivalents based on the epoxy group of the epoxy resin. Since curing performance becomes excellent when the content of the reaction group becomes 1 equivalent based on the epoxy group though it differs according to the type of the curing agent, the above total content is preferably 0.3 to 3 equivalents, more preferably 0.5 to 2 equivalents.

The reaction group refers to a group able to react with an epoxy group. When one group can react with two epoxy groups, the group is counted as two reaction groups. For example, since an amino group (—NH$_2$) can react with two epoxy groups, it is counted as two reaction groups.

As the curing accelerator, known compounds which are used as a curing accelerator at the time of producing a cured resin may be used. Examples of the curing accelerator include imidazoles such as 2-ethyl-4-methylmidazole and 1-methylimidazole; tertiary amines such as benzyl dimethylamine and N,N-dimethylaniline; quaternary ammonium salts such as tetramethylammonium chloride and benzyl triethylammonium chloride; phosphonium salts such as tetra-n-butyl phosphonium-o,o-diethylphosphorodithionate and tetrabutyl phosphonium benzotriazolate; metal salts such as zinc octylate and zinc stearate; and metal complexes such as zinc acetyl acetone and zinc benzoyl acetone.

The content of the curing accelerator is not particularly limited but preferably 0.01 to 5 parts by weight based on 100 parts by weight of the total of the epoxy resin and the curing agent. When the content of the curing accelerator is lower than 0.01 part by weight, an acceleration effect may not be obtained. When the content is higher than 5 parts by weight, curing is accelerated, whereby handling may become worse at the time of curing the thermosetting resin composition. From this point of view, the content is more preferably 0.05 to 3 parts by weight, much more preferably 0.1 to 1.5 parts by weight.

The difference between the glass transition temperature of a cured resin obtained from the thermosetting resin composition of the present invention after 2 hours of curing (Tg·2H) and the glass transition temperature of a cured resin obtained from the thermosetting resin composition after 4 hours of curing (Tg·4H) is preferably less than 10° C. at a thermal curing temperature of 160 to 200° C.

This is due to the fact that the polyvalent amine-based curing agent (component b) readily reacts with an epoxy group at the above curing temperature range and has a tetravalent amino group, thereby improving its affinity for the epoxy resin as the number of reacted amino groups increases, with the result that curing proceeds acceleratedly and a high crosslink density is achieved in a short time. Therefore, the difference between Tg·2H and Tg·4H can be made less than 10° C. at the above curing temperature range.

The thermosetting resin composition of the present invention may have a (Tg·160° C./4H) of 175° C. or higher and a (Tg·180° C./2H) of 185° C. or higher. This is because the polyvalent amine-based curing agent (component b) achieves a high crosslink density in a short time and provides high heat resistance due to the tetravalent amino group and the skeleton as described above. Therefore, a high glass transition temperature Tg can be achieved in a short time at the above thermal curing temperature.

The thermosetting resin composition of the present invention has a satisfactory pot life from the viewpoint of handling. Since the polyvalent amine-based curing agent (component b) of the present invention retains a certain molecular weight, it can suppress movability in the epoxy resin as compared with a polyvalent amine having a low molecular weight. Further, since it is a compound having a tetravalent amino group, the number of molecules for the epoxy resin is generally smaller than that of another amine compound. Therefore, after it is mixed with the epoxy resin, it can be stored without gelling at a low temperature of 10 to 25° C. for a relatively long time. Since the polyvalent amine-based curing agent (component b) readily reacts with an epoxy group at a curing temperature higher than 100° C. and has a tetravalent amino group, its affinity for the epoxy resin improves as the number of reacted amino groups increases and curing can proceed acceleratedly. Therefore, the polyvalent amine-based curing agent can be used for a wide range of applications without restriction and can achieve high curing performance.

The thermosetting resin composition of the present invention may comprise additives as required as long as they are not adverse to the object of the present invention in addition to the epoxy resin (component A) and the polyvalent amine-based curing agent (component b).

The additives include an inorganic filler; coupling agent such as silane coupling agent, titanate coupling agent, aluminum coupling agent or aluminum/zirconium coupling agent; flame retardant such as brominated epoxy resin, antimony oxide or phosphorus compound; inorganic ion exchanger such as bismuth oxide hydrate; coloring agent such as carbon black or red oxide; silicone oil; silicone-based or rubber-based stress reducing agent; release agent such as natural wax, synthetic wax, higher fatty acid, metal salt thereof or paraffin; antioxidant; and carbodiimide compound. When a carbodiimide is used, carbodiimides described in WO2010/071213 may be advantageously used.

The thermosetting resin composition of the present invention may be advantageously used for applications in which heat resistance is required, for example, semiconductor sealing materials, prepregs and composite matrix materials, printed circuit boards, laminate sheets, electrical insulating materials and pastes.

<Process for Producing Thermosetting Resin Composition>

The thermosetting resin composition of the present invention may be produced by a known process. For example, the resin composition can be prepared by mixing together the epoxy resin (component A), the polyvalent amine-based curing agent (component b), the other curing agent (component C), the curing accelerator and other additives by means of a mixer. The mixing method is not particularly limited and a conventionally known method may be used. A solution state or molten state is preferred from the viewpoint of homogeneity. As another mixing method, a method in which a master batch epoxy resin is used or a method in which impregnation is carried out by contact may be used. After mixing, the mixture is kneaded under heating by means of a kneading machine such as a roll, kneader or extruder, cooled and pulverized as required to obtain a resin composition as a solid component.

To prepare the resin composition as a solution, various solvents may be used but a solvent which is inactive to the epoxy resin (component A), the polyvalent amine-based curing agent (component b), the other curing agent, the curing accelerator and other additives and dissolves some or all of these components may be advantageously used. Examples of the solvent include hydrocarbon-based solvents, ketone-based solvents, ester-based solvents, ether-based solvents, halogen-based solvents and amide-based solvents.

The hydrocarbon-based solvents include hexane, cyclohexane, benzene, toluene, xylene, heptane and decane. The ketone-based solvents include acetone, methyl ethyl ketone, diethyl ketone, cyclohexanone and isophorone. The ester-based solvents include ethyl acetate, methyl acetate, ethyl succinate, methyl carbonate, ethyl benzoate and diethylene glycol diacetate. The ether-based solvents include diethyl ether, dibutyl ether, tetrahydrofuran, dioxane, diethylene glycol dimethyl ether, triethylene glycol diethyl ether and diphenyl ether.

The halogen-based solvents include dichloromethane, chloroform, tetrachloromethane, dichloroethane, 1,1',2,2'-tetrachloroethane, chlorobenzene and dichlorobenzene. The amide-based solvents include formamide, dimethyl formamide, dimethyl acetamide and N-methylprrolidone. These solvents may be used alone or as a mixed solvent as desired.

The thermosetting resin composition of the present invention may be processed by a generally known method according to each application. Processing is not particularly limited but includes molding, coating and impregnation.

To manufacture a semiconductor device by using the thermosetting resin composition of the present invention to seal an electronic part such as a semiconductor element, the thermosetting resin composition should be cured and molded by a molding method such as transfer molding, compression molding or injection molding.

To manufacture a prepreg, the thermosetting resin composition of the present invention should be impregnated as resin varnish into a base material. The resin varnish is a mixture of the epoxy resin, the polyvalent amine-based curing agent, the other curing agent, the curing accelerator and other additives or a solution prepared by dissolving these in a solvent. As the base material, an organic fiber such as glass cloth, carbon fiber or aramid may be used.

Further, to manufacture metal foil with a resin, a method in which the thermosetting resin composition of the present invention as resin varnish is applied to metal foil by a known method, such as methods with a comma coater, knife coater or curtain coater and a volatile component such as a solvent is dried and removed to form a resin layer by half curing the thermosetting resin composition of the present invention may be employed.

<Curing Method>

A known method may be used to cure the thermosetting resin composition of the present invention. Basically, by heating at a curing temperature suitable for the epoxy resin and the curing agent in use, a satisfactory cure degree is obtained.

Further, when the polyvalent amine-based curing agent (component b) represented by the formula (b-i) is used, as compared with a case where another general curing agent is used, satisfactory curing performance may be obtained in a short time or at a low temperature, whereby the suppression of the thermal deterioration of components such as the epoxy resin by a long-term treatment or high-temperature treatment can be expected.

To manufacture a cured resin having a glass transition temperature Tg higher than 180° C. after the thermal curing of the thermosetting resin composition, when an ordinary curing agent is used, curing is carried out at 180° C., or when curing is carried out at a temperature lower than 180° C., a long curing time is needed. When the polyvalent amine-based curing agent (component b) represented by the formula (b-i) is used, a cured resin having a glass transition temperature Tg higher than 180° C. is obtained in a short time if the resin composition is cured at a temperature lower than 180° C. Therefore, the curing shrinkage becomes small at the time of thermal curing, thereby making it possible to enhance the dimensional accuracy of a product after thermal curing. Further, a cured resin having excellent mechanical properties such as strength may be obtained since the thermal deterioration of the epoxy resin is suppressed.

The curing temperature of the thermosetting resin composition of the present invention which greatly differs according to the epoxy resin and the curing agent in use is preferably selected from a range from 25° C. to 250° C. When the curing temperature is lower than 25° C., the thermosetting resin composition may not cure completely. When the curing temperature is higher than 250° C., curing proceeds but the thermosetting resin composition itself deteriorates by heat and satisfactory curing performance may not be obtained. From this point of view, the curing temperature is more preferably 40 to 225° C., much more preferably 50 to 200° C.

<Cured Resin>

The cured resin in the present invention comprises a compound represented by the following formula (b-ii).

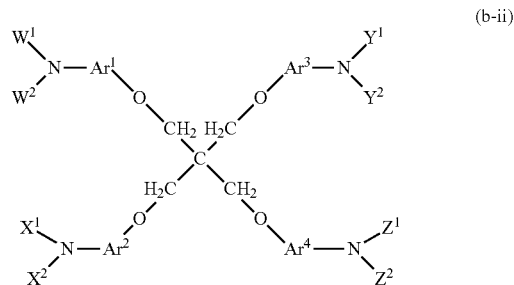

(wherein $Ar^1$ to $Ar^4$ are each independently a phenylene group or naphthalene-diyl group which may be substituted by a substituent. $W^1$, $W^2$, $X^1$, $X^2$, $Y^1$, $Y^2$, $Z^1$ and $Z^2$ are each independently selected from a hydrogen atom and group represented by the following formula (b-iii), with the proviso that at least two out of $W^1$, $W^2$, $X^1$, $X^2$, $Y^1$, $Y^2$, $Z^1$ and $Z^2$ are groups represented by the following formula (b-iii))

(wherein the wavy part represents an epoxy resin residue)

$Ar^1$ to $Ar^4$ are each independently a phenylene group or naphthalene-diyl group which may be substituted by a substituent. The substituent is an aliphatic group having 1 to 20 carbon atoms, alicyclic group having 3 to 20 carbon atoms, aromatic group having 5 to 15 carbon atoms, halogen atom, nitro group, amide group, hydroxyl group, ester group, ether group, aldehyde group or a combination thereof.

An alkyl group having 1 to 20 carbon atoms is given as an example of the aliphatic group. Examples of the alkyl group having 1 to 20 carbon atoms include methyl group, ethyl group, propyl group, butyl group, pentyl group, hexyl group, heptyl group, octyl group, nonyl group, decyl group, dodecyl group and hexadecyl group.

A cycloalkyl group having 3 to 20 carbon atoms is given as an example of the alicyclic group. Examples of the cycloalkyl group having 3 to 20 carbon atoms include cyclopropyl group, cyclobutyl group, cyclopentyl group, cyclohexyl group, cycloheptyl group, cyclooctyl group, cyclononyl group, cyclodecyl group, cyclododecyl group and cyclohexadecyl group.

An aryl group having 5 to 15 carbon atoms, which may have a heterocyclic structure containing a hetero atom, is given as an example of the aromatic group. Examples of the aryl group having 5 to 15 carbon atoms include phenyl group and naphthyl group.

W¹, W², X¹, X², Y¹, Y², Z¹ and Z² are each independently selected from a hydrogen atom and group represented by the following formula (b-iii).

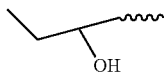

(b-iii)

(wherein the wavy part represents an epoxy resin residue.)

The above compound may be obtained as a reaction product between the epoxy resin (component A) and the polyvalent amine-based curing agent (component b) represented by the above chemical formula (b-i). As the proportion of this reaction increases, W¹, W², X¹, X², Y¹, Y², Z¹ and Z² are substituted from the hydrogen atom to the group of the above formula (b-iii). At least two groups of the above formula (b-iii) should be contained in the compound to produce the cured resin. Therefore, at least two out of W¹, W², X¹, X², Y¹, Y², Z¹ and Z² need to be the groups of the above formula (b-iii).

The epoxy resin residue is a group obtained by removing the terminal epoxy group of the above epoxy resin (component A).

The cured resin of the present invention has a content of the compound represented by the above formula (b-ii) of preferably not less than 50 wt %, especially from the viewpoint of obtaining desired performance, more preferably not less than 65 wt %, much more preferably not less than 80 wt % based on the total weight. The above cured resin can be easily obtained by curing the thermosetting epoxy resin of the present invention, and curing may be carried out by the above-described method.

EXAMPLES

The following examples are provided to further illustrate the present invention. Characteristic properties were measured by the following methods.

(1) NMR Identification of Cyclic Carbodiimide Structure:

The synthesized cyclic carbodiimide compound was checked by ¹H-NMR and ¹³C-NMR. The JNR-EX270 NMR of JEOL Ltd. was used. Heavy chloroform was used as a solvent.

(2) IR Identification of Carbodiimide Skeleton of Cyclic Carbodiimide:

The existence and nonexistence of the carbodiimide skeleton of the synthesized cyclic carbodiimide compound were checked at 2,100 to 2,200 cm⁻¹ which is characteristic to carbodiimide by FT-IR. The Magna-750 FT-IR of Thermo Fisher Scientific was used.

(3) Measurement of Glass Transition Temperature (Tg) of Cured Resin:

DSC (TA-2920 of TA Instruments) was used to heat a cured sample (cured resin) up to 250° C. at a rate of 10° C./min in a nitrogen air stream in a first cycle so as to measure its glass transition temperature (Tg).

Compounds used in Examples are described below.

The following resins were used as the epoxy resin (component A).

A1: jER (registered trademark) 828 bisphenol A type epoxy resin of Mitsubishi Chemical Corporation A2: YDCN-700-5 o-cresol novolak type epoxy resin of Nippon Steel & Sumitomo Metal Corporation A3: jER (registered trademark) 806 bisphenol F type epoxy resin of Mitsubishi Chemical Corporation A4: YX4000 biphenyl type epoxy resin of Mitsubishi Chemical Corporation The following compound was manufactured and used as the cyclic carbodiimide compound (component B).

<Production Example 1> Synthesis of Polyvalent Cyclic Carbodiimide (B)

B: Mw=516

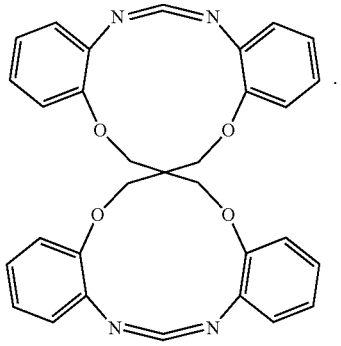

(B-v)

o-nitrophenol (0.11 mol), pentaerythrityl tetrabromide (0.025 mol), potassium carbonate (0.33 mol) and 200 ml of N,N-dimethyl formamide were fed to a reactor equipped with a stirrer and a heater in an N₂ atmosphere to carry out a reaction at 130° C. for 12 hours, DMF was removed under reduced pressure, the obtained solid matter was dissolved in 200 ml of dichloromethane, and separation was carried out three times with 100 ml of water. An organic layer was dehydrated with 5 g of sodium sulfate, and dichloromethane was removed under reduced pressure to obtain an intermediate product D (nitro compound).

Then, the intermediate product D (0.1 mol), 5% palladium carbon (Pd/C) (2 g) and 400 ml of ethanol/dichloromethane (70/30) were fed to a reactor equipped with a stirrer, hydrogen substitution was carried out five times to carry out a reaction at 25° C. while hydrogen was always supplied, and the reaction was terminated when hydrogen was not reduced any more. When Pd/C was collected to remove the mixed solvent, an intermediate product E (amine compound) was obtained.

Then, triphenylphosphine dibromide (0.11 mol) and 150 ml of 1,2-dichloroethane were fed to a reactor equipped with a stirrer, a heater and a dropping funnel in a nitrogen atmosphere and stirred. A solution prepared by dissolving the intermediate product E (0.025 mol) and triethylamine (0.25 mol) in 50 ml of 1,2-dichloroethane was added dropwise to the resulting solution gently at 25° C. After the end of addition, a reaction was carried out at 70° C. for 5 hours. Thereafter, the reaction solution was filtered, and the filtrate was separated five times with 100 ml of water. An organic layer was dehydrated with 5 g of sodium sulfate, and 1,2-dichloroethane was removed under reduced pressure to obtain an intermediate product F (triphenylphosphine compound).

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an N₂ atmosphere and stirred. A solution prepared by dissolving the intermediate product F (0.025 mol) in 100 ml of dichloromethane was added dropwise to the resulting solution gently at 25° C. After the end of addition, a reaction was carried out for 12 hours.

Thereafter, a solid material obtained by removing dichloromethane was purified to obtain B. The structure of B was checked by NMR and IR.

The following compounds and resins were used as the other curing agent (component C) and the curing accelerator (component D).

C1: YH-306 acid anhydride of Mitsubishi Chemical Corporation
C2: 3,3'-diaminodiphenyl sulfone of Wako Pure Chemical Industries, Ltd.
C3: TD-2106 novolak resin of Nippon Steel & Sumitomo Metal Corporation
C4: Carbodilite (registered trademark) LA-1 carbodiimide compound of Nisshinbou Chemical Inc.
C5: Kayahard (registered trademark) A-A aromatic diamine of Nippon Kayaku Co., Ltd.
C6: MEH-8000H liquid phenol resin of Meiwa Plastic Industries, Ltd.
C7: jER (registered trademark) Cure W aromatic diamine of Mitsubishi Chemical Corporation
C8: WONDAMINE (registered trademark) HM alicyclic diamine of New Japan Chemical Co., Ltd.
D1: 2-ethyl-4-methylimidazole of Wako Pure Chemical Industries, Ltd.
D2: triphenylphosphine of Wako Pure Chemical Industries, Ltd.
D3: Carbodilite (registered trademark) LA-1 carbodiimide compound of Nisshinbo Chemical Inc.

The above compounds and resins were each independently dried under reduced pressure at 25° C. for 5 hours before use.

Effect as Resin Curing Agent

Example 1

The numbers of parts by weight shown in Table 1 of A1, B, C1 and D1 were mixed together, and the resulting mixture in a molten state was fed to a 30 ml-scale screw tubular bottle, heated until the inside temperature of the ON-300S constant-temperature drier (of AS One Corporation) became 80° C., taken out and stirred well with a stirrer. This operation was repeated three times to produce a homogeneous thermosetting resin composition.

1 g of this thermosetting resin composition was set on a Teflon-coated stainless plate and cured at 150° C. for 0.5 hour by using the ON-300S constant-temperature drier (of AS One Corporation). Tg of the obtained sample is shown in Table 1.

Comparative Example 1

A cured resin was produced by curing at 150° C. for 0.5 hour in the same manner as in Example 1 except that B was removed from the resin composition. Tg of the obtained sample is shown in Table 1.

Comparative Example 2

A cured resin was produced by curing at 150° C. for 0.5 hour in the same manner as in Example 1 except that B was changed to C4 and the content of C4 was set as shown in Table 1. Tg of the obtained sample is shown in Table 1.

Example 2

The numbers of parts by weight shown in Table 1 of A1, B and C2 were mixed together, and the resulting mixture in a molten state was fed to a 30 ml-scale screw tubular bottle, heated until the inside temperature of the ON-300S constant-temperature drier (of AS One Corporation) became 80° C., taken out and stirred well with a stirrer. This operation was repeated three times to produce a homogeneous thermosetting resin composition.

1 g of this thermosetting resin composition was set on a Teflon-coated stainless plate and cured at 160° C. for 2 hours by using the ON-300S constant-temperature drier (of AS One Corporation). Tg of the obtained sample is shown in Table 1.

Comparative Example 3

A cured resin was produced by curing at 160° C. for 2 hours in the same manner as in Example 2 except that B was removed from the resin composition. Tg of the obtained sample is shown in Table 1.

Example 3

The numbers of parts by weight shown in Table 1 of A2, B, C3 and D2 were mixed together, the resulting mixture in a solid state was fed to a 30 ml-scale screw tubular bottle, heated until the inside temperature of the ON-300S constant-temperature drier (of AS One Corporation) became 120° C. and taken out, and the obtained mixture in a molten state was stirred well with a stirrer. This operation was repeated three times to produce a homogeneous resin composition. 1 g of this resin composition was set on a Teflon-coated stainless plate and cured at 175° C. for 8 hours by using the ON-300S constant-temperature drier (of AS One Corporation). Tg of the obtained sample is shown in Table 1.

Comparative Example 4

A cured resin was produced by curing at 175° C. for 8 hours in the same manner as in Example 3 except that B was removed from the resin composition. Tg of the obtained sample is shown in Table 1.

Effect as Curing Accelerator

Example 4

The numbers of parts by weight shown in Table 1 of A2, C3 and B were mixed together, the resulting mixture in a solid state was fed to a 30 ml-scale screw tubular bottle, heated until the inside temperature of the ON-300S constant-temperature drier (of AS One Corporation) became 120° C. and taken out, and the obtained mixture in a molten state was stirred well with a stirrer. This operation was repeated three times to produce a homogeneous thermosetting resin composition.

1 g of this thermosetting resin composition was set on a Teflon-coated stainless plate and cured at 200° C. for 5 hours by using the ON-300S constant-temperature drier (of AS One Corporation). Tg of the obtained sample is shown in Table 1.

Examples 5 to 7

Cured resins were produced by curing at 200° C. for 5 hours in the same manner as in Example 4 except that the number of parts by weight of B was changed as shown in Table 1. Tg's of the obtained samples are shown in Table 1.

Comparative Example 5

A cured resin was produced by curing at 200° C. for 5 hours in the same manner as in Example 4 except that B was removed from the resin composition. Tg of the obtained sample is shown in Table 1.

Comparative Examples 6 and 7

Cured resins were produced by curing at 200° C. for 5 hours in the same manner as in Example 4 except that B was changed to D3 and the content of D3 was set as shown in Table 1. Tg's of the obtained samples are shown in Table 1.

Example 8

The numbers of parts by weight shown in Table 1 of A2 and B were mixed together, the resulting mixture in a solid state was fed to a 30 ml-scale screw tubular bottle, heated until the inside temperature of the ON-300S constant-temperature drier (of AS One Corporation) became 150° C. and taken out every 10 minutes, and the obtained mixture in a molten state was stirred well with a stirrer. This operation was repeated six times to obtain a homogeneous molten epoxy resin. The number of parts by weight shown in Table 1 of C3 was added to the resin and heated until the inside temperature of the ON-300S constant-temperature drier (of AS One Corporation) became 120° C. and taken out, and the obtained mixture in a molten state was stirred well with a stirrer. This operation was repeated three times to produce a homogeneous thermosetting resin composition.

1 g of this thermosetting resin composition was set on a Teflon-coated stainless plate and cured at 200° C. for 5 hours by using the ON-300S constant-temperature drier (of AS One Corporation). Tg of the obtained sample is shown in Table 1.

Example 9

A cured resin was produced by curing at 200° C. for 5 hours in the same manner as in Example 8 except that the number of parts by weight of B was changed as shown in Table 1. Tg of the obtained sample is shown in Table 1.

Example 10

The numbers of parts by weight shown in Table 1 of A1, B and C5 were mixed together, and the resulting mixture in a slurry state was fed to a 30 ml-scale screw tubular bottle, heated until the inside temperature of the ON-300S constant-temperature drier (of AS One Corporation) became 80° C., taken out and stirred well with a stirrer to produce a homogeneous thermosetting resin composition.

1 g of this thermosetting resin composition was set on a Teflon-coated stainless plate and cured at 160° C. for 2 hours by using the ON-300S constant-temperature drier (of AS One Corporation). Tg of the obtained sample is shown in Table 1.

Example 11

A cured resin was produced by curing at 160° C. for 2 hours in the same manner as in Example 10 except that the number of parts by weight of B was changed as shown in Table 1. Tg of the obtained sample is shown in Table 1.

Example 12

The numbers of parts by weight shown in Table 1 of A1 and B were mixed together, and the resulting mixture in a slurry state was fed to a 30 ml-scale screw tubular bottle, heated until the inside temperature of the ON-300S constant-temperature drier (of AS One Corporation) became 180° C., taken out every 10 minutes and stirred well with a stirrer. This operation was repeated four times to obtain a homogeneous epoxy resin. The number of parts by weight shown in Table 1 of C5 was added to this resin and heated until the inside temperature of the ON-300S constant-temperature drier (of AS One Corporation) became 80° C., taken out and stirred well with a stirrer to produce a homogeneous thermosetting resin composition.

1 g of this thermosetting resin composition was set on a Teflon-coated stainless plate and cured at 160° C. for 2 hours by using the ON-300S constant-temperature drier (of AS One Corporation). Tg of the obtained sample is shown in Table 1.

Comparative Example 8

A cured resin was produced by curing at 160° C. for 2 hours in the same manner as in Example 10 except that B was removed from the resin composition. Tg of the obtained sample is shown in Table 1.

Example 13

The numbers of parts by weight shown in Table 1 of A1, B, C6 and D1 were mixed together, and the resulting mixture in a slurry state was fed to a 30 ml-scale screw tubular bottle, heated until the inside temperature of the ON-300S constant-temperature drier (of AS One Corporation) became 80° C., taken out and stirred well with a stirrer to produce a homogeneous thermosetting resin composition.

1 g of this thermosetting resin composition was set on a Teflon-coated stainless plate and cure at 160° C. for 6 hours by using the ON-300S constant-temperature drier (of AS One Corporation). Tg of the obtained sample is shown in Table 1.

Comparative Example 9

A cured resin was produced by curing at 160° C. for 6 hours in the same manner as in Example 13 except that B was removed from the resin composition. Tg of the obtained sample is shown in Table 1.

Example 14

The numbers of parts by weight shown in Table 1 of A3, B and C7 were mixed together, and the resulting mixture in a slurry state was fed to a 30 ml-scale screw tubular bottle, heated until the inside temperature of the ON-300S constant-temperature drier (of AS One Corporation) became 80° C., taken out and stirred well with a stirrer to produce a homogeneous thermosetting resin composition.

1 g of this thermosetting resin composition was set on a Teflon-coated stainless plate and cured at 165° C. for 2 hours by using the ON-300S constant-temperature drier (of AS One Corporation). Tg of the obtained sample is shown in Table 1.

Comparative Example 10

A cured resin was produced by curing at 165° C. for 2 hours in the same manner as in Example 14 except that B was removed from the resin composition. Tg of the obtained sample is shown in Table 1.

Example 15

The numbers of parts by weight shown in Table 1 of A3, B and C8 were mixed together, and the resulting mixture in a slurry state was fed to a 30 ml-scale screw tubular bottle, heated until the inside temperature of the ON-300S constant-temperature drier (of AS One Corporation) became 80° C., taken out and stirred well with a stirrer to produce a homogeneous thermosetting resin composition.

1 g of this thermosetting resin composition was set on a Teflon-coated stainless plate and cured at 165° C. for 2 hours by using the ON-300S constant-temperature drier (of AS One Corporation). Tg of the obtained sample is shown in Table 1.

Comparative Example 11

A cured resin was produced by curing at 165° C. for 2 hours in the same manner as in Example 15 except that B was removed from the resin composition. Tg of the obtained sample is shown in Table 1.

Example 16

The numbers of parts by weight shown in Table 1 of A4, B, C3 and D2 were mixed together, and the resulting mixture in a solid state was fed to a 30 ml-scale screw tubular bottle, heated until the inside temperature of the ON-300S constant-temperature drier (of AS One Corporation) became 120° C., taken out and stirred well with a stirrer. This operation was repeated three times to produce a homogeneous thermosetting resin composition.

1 g of this thermosetting resin composition was set on a Teflon-coated stainless plate and cure at 180° C. for 5 hours by using the ON-300S constant-temperature drier (of AS One Corporation). Tg of the obtained sample is shown in Table 1.

Comparative Example 12

A cured resin was produced by curing at 180° C. for 5 hours in the same manner as in Example 16 except that B was removed from the resin composition. Tg of the obtained sample is shown in Table 1.

Example 17

The numbers of parts by weight shown in Table 1 of A2, B, C3 and D2 were mixed together, and the resulting mixture in a solid state was fed to a 30 ml-scale screw tubular bottle, heated until the inside temperature of the ON-300S constant-temperature drier (of AS One Corporation) became 120° C., taken out and stirred well with a stirrer. This operation was repeated three times to produce a homogeneous thermosetting resin composition.

1 g of this thermosetting resin composition was set on a Teflon-coated stainless plate and cured at 180° C. for 5 hours by using the ON-300S constant-temperature drier (of AS One Corporation). Tg of the obtained sample is shown in Table 1.

Example 18

A cured resin was produced by curing at 180° C. for 5 hours in the same manner as in Example 17 except that the number of parts by weight of B was changed as shown in Table 1. Tg of the obtained sample is shown in Table 1.

Comparative Example 13

A cured resin was produced by curing at 180° C. for 5 hours in the same manner as in Example 17 except that B was removed from the resin composition. Tg of the obtained sample is shown in Table 1.

TABLE 1

|  |  |  | Unit | Ex. 1 | C. Ex. 1 | C. Ex. 2 | Ex. 2 | C. Ex. 3 | Ex. 3 | C. Ex. 4 | Ex. 4 |
|---|---|---|---|---|---|---|---|---|---|---|---|
| Thermo-setting resin compo-sition | Epoxy resin | A1 | parts by weight | 100 | 100 | 100 | 100 | 100 |  |  |  |
|  |  | A2 | parts by weight |  |  |  |  |  | 100 | 100 | 100 |
|  |  | A3 | parts by weight |  |  |  |  |  |  |  |  |
|  |  | A4 | parts by weight |  |  |  |  |  |  |  |  |
|  | Cyclic carbodiimide compound | B | parts by weight | 4.4 |  |  | 2.7 |  | 3.0 |  | 1.5 |
|  | Other curing agent | C1 | parts by weight | 120 | 120 | 120 |  |  |  |  |  |
|  |  | C2 | parts by weight |  |  |  | 34.9 | 34.9 |  |  |  |
|  |  | C3 | parts by weight |  |  |  |  |  | 51 | 51 | 51 |
|  |  | C4 | parts by weight |  |  |  | 4.4 |  |  |  |  |
|  |  | C5 | parts by weight |  |  |  |  |  |  |  |  |
|  |  | C6 | parts by weight |  |  |  |  |  |  |  |  |
|  |  | C7 | parts by weight |  |  |  |  |  |  |  |  |
|  |  | C8 | parts by weight |  |  |  |  |  |  |  |  |
|  | Curing accelerator | D1 | parts by weight | 2.2 | 2.2 | 2.2 |  |  |  |  |  |
|  |  | D2 | parts by weight |  |  |  |  |  | 0.15 | 0.15 |  |
|  |  | D3 | parts by weight |  |  |  |  |  |  |  |  |
| Curing temperature |  |  | ° C. | 150 | 150 | 150 | 160 | 160 | 175 | 175 | 200 |
| Curing time |  |  | Hour | 0.5 | 0.5 | 0.5 | 4 | 4 | 8 | 8 | 5 |
| Glass transition temperature(Tg) |  |  | ° C. | 143.1 | 136.6 | 140.2 | 173.9 | 167.9 | 192.8 | 182.1 | 108 |

TABLE 1-continued

| | | | Unit | Ex. 5 | Ex. 6 | Ex. 7 | C. Ex. 5 | C. Ex. 6 | C. Ex. 7 | Ex. 8 | Ex. 9 |
|---|---|---|---|---|---|---|---|---|---|---|---|
| Thermo- setting resin compo- sition | Epoxy resin | A1 | parts by weight | | | | | | | | |
| | | A2 | parts by weight | 100 | 100 | 100 | 100 | 100 | 100 | 100 | 100 |
| | | A3 | parts by weight | | | | | | | | |
| | | A4 | parts by weight | | | | | | | | |
| | Cyclic carbodiimide compound | B | parts by weight | 4.5 | 7.5 | 15 | | | | 7.5 | 15 |
| | Other curing agent | C1 | parts by weight | | | | | | | | |
| | | C2 | parts by weight | | | | | | | | |
| | | C3 | parts by weight | 51 | 51 | 51 | 51 | 51 | 51 | 51 | 51 |
| | | C4 | parts by weight | | | | | | | | |
| | | C5 | parts by weight | | | | | | | | |
| | | C6 | parts by weight | | | | | | | | |
| | | C7 | parts by weight | | | | | | | | |
| | | C8 | parts by weight | | | | | | | | |
| | Curing accelerator | D1 | parts by weight | | | | | | | | |
| | | D2 | parts by weight | | | | | | | | |
| | | D3 | parts by weight | | | | | 4.5 | 15 | | |
| Curing temperature | | | ° C. | 200 | 200 | 200 | 200 | 200 | 200 | 200 | 200 |
| Curing time | | | Hour | 5 | 5 | 5 | 5 | 5 | 5 | 5 | 5 |
| Glass transition temperature(Tg) | | | ° C. | 128.4 | 150.7 | 206.1 | 101.2 | 105.7 | 105.3 | 156.7 | 215.1 |

| | | | Unit | Ex. 10 | Ex. 11 | Ex. 12 | C. Ex. 8 | Ex. 13 | C. Ex. 9 | Ex. 14 | C. Ex. 10 |
|---|---|---|---|---|---|---|---|---|---|---|---|
| Thermo- setting resin compo- sition | Epoxy resin | A1 | parts by weight | 100 | 100 | 100 | 100 | 100 | 100 | | |
| | | A2 | parts by weight | | | | | | | | |
| | | A3 | parts by weight | | | | | | | 100 | 100 |
| | | A4 | parts by weight | | | | | | | | |
| | Cyclic carbodiimide compound | B | parts by weight | 5 | 10 | 10 | | 10 | | 12.7 | |
| | Other curing agent | C1 | parts by weight | | | | | | | | |
| | | C2 | parts by weight | | | | | | | | |
| | | C3 | parts by weight | | | | | | | | |
| | | C4 | parts by weight | | | | | | | | |
| | | C5 | parts by weight | 34 | 34 | 34 | 34 | | | | |
| | | C6 | parts by weight | | | | | 38 | 38 | | |
| | | C7 | parts by weight | | | | | | | 27 | 27 |
| | | C8 | parts by weight | | | | | | | | |
| | Curing accelerator | D1 | parts by weight | | | | | 2 | 2 | | |
| | | D2 | parts by weight | | | | | | | | |
| | | D3 | parts by weight | | | | | | | | |
| Curing temperature | | | ° C. | 160 | 160 | 160 | 160 | 160 | 160 | 165 | 165 |
| Curing time | | | Hour | 2 | 2 | 2 | 2 | 6 | 6 | 2 | 2 |
| Glass transition temperature(Tg) | | | ° C. | 135.7 | 140.19 | 145 | 128 | 105.6 | 96.4 | 145.2 | 130.4 |

| | | | Unit | Ex. 15 | C. Ex. 11 | Ex. 16 | C. Ex. 12 | Ex. 17 | Ex. 18 | C. Ex. 13 |
|---|---|---|---|---|---|---|---|---|---|---|
| Thermo- setting resin compo- sition | Epoxy resin | A1 | parts by weight | | | | | | | |
| | | A2 | parts by weight | | | | | 100 | 100 | 100 |
| | | A3 | parts by weight | 100 | 100 | | | | | |
| | | A4 | parts by weight | | | 100 | 100 | | | |
| | Cyclic carbodiimide compound | B | parts by weight | 13.2 | | 15 | | 7.5 | 15 | |
| | Other curing agent | C1 | parts by weight | | | | | | | |
| | | C2 | parts by weight | | | | | | | |
| | | C3 | parts by weight | | | 55.9 | 55.9 | 51 | 51 | 51 |
| | | C4 | parts by weight | | | | | | | |
| | | C5 | parts by weight | | | | | | | |
| | | C6 | parts by weight | | | | | | | |
| | | C7 | parts by weight | | | | | | | |
| | | C8 | parts by weight | 32 | 32 | | | | | |
| | Curing accelerator | D1 | parts by weight | | | 0.15 | 0.15 | 0.15 | 0.15 | 0.15 |
| | | D2 | parts by weight | | | | | | | |
| | | D3 | parts by weight | | | | | | | |
| Curing temperature | | | ° C. | 165 | 165 | 180 | 180 | 180 | 180 | 180 |
| Curing time | | | Hour | 2 | 2 | 5 | 5 | 5 | 5 | 5 |
| Glass transition temperature(Tg) | | | ° C. | 147.8 | 132.9 | 185.1 | 137.4 | 196.4 | 204.5 | 184.1 |

Ex.: Example
C. Ex.: Comparative Example

It is understood from these results that when the cyclic carbodiimide compound is used as a curing agent or curing accelerator, Tg improves as compared with a case where a resin composition comprising no cyclic carbodiimide compound is cured under the same conditions. It is also understood that the effect of this cyclic carbodiimide compound is higher than those of other carbodiimide compounds. It is further understood that a cured resin comprising the cyclic carbodiimide compound achieves high Tg in a short time even when the curing temperature is low.

Examples 19 to 25, Comparative Examples 14 to 25

Characteristic properties were measured by the following methods.
(1) NMR Identification of Chemical Structures of Polyvalent Amine-Based Curing Agent (Component b) and Cyclic Carbodiimide (cc1):
The synthesized polyvalent amine compound was checked by $^1$H-NMR and $^{13}$C-NMR. The JNR-EX270 NMR of JEOL Ltd. was used. Heavy chloroform was used as a solvent.
(2) Measurement of Glass Transition Temperature (Tg) of Cured Resin:
The produced cured resin was heated up to 250° C. at a rate of 10° C./min in a nitrogen air stream in a first cycle to measure its glass transition temperature (Tg) by using DSC (TA-2920 of TA Instruments).
(3) IR Identification of Carbodiimide Skeleton of Cyclic Carbodiimide:
The existence and nonexistence of the carbodiimide skeleton of the synthesized cyclic carbodiimide compound were checked at 2,100 to 2,200 cm$^{-1}$ which is characteristic to carbodiimide by FT-IR. The Magna-750 FT-IR of Thermo Fisher Scientific was used.
The following resin was used as the epoxy resin (component A).
a1: jER (registered trademark) 828 bisphenol A type epoxy resin of Mitsubishi Chemical Corporation
The following compound was manufactured and used as the polyvalent amine-based curing agent (component b).

<Production Example 1> Synthesis of Polyvalent Amine-Based Curing Agent (b1)

b1: Mw=501

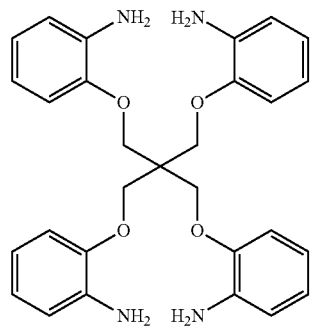 [SMILES: Nc1ccccc1OCC(COc1ccccc1N)(COc1ccccc1N)COc1ccccc1N]

o-nitrophenol (0.11 mol), pentaerythrityl tetrabromide (0.025 mol), potassium carbonate (0.33 mol) and 200 ml of N,N-dimethyl formamide were fed to a reactor equipped with a stirrer and a heater in an N$_2$ atmosphere to carry out a reaction at 130° C. for 12 hours, DMF was removed under reduced pressure, the obtained solid matter was dissolved in 200 ml of dichloromethane, and separation was carried out three times with 100 ml of water. An organic layer was dehydrated with 5 g of sodium sulfate, and dichloromethane was removed under reduced pressure to obtain an intermediate product C (nitro compound).
Then, the intermediate product C (0.1 mol), 5% palladium carbon (Pd/C) (2 g) and 400 ml of ethanol/dichloromethane (70/30) were fed to a reactor equipped with a stirrer, hydrogen substitution was carried out five times to carry out a reaction at 25° C. while hydrogen was always supplied, and the reaction was terminated when hydrogen was not reduced any more. A solid matter obtained by collecting Pd/C and removing the mixed solvent was purified to obtain B1. The structure of b1 was checked by NMR. The following compound was used as the other curing agent.

<Production Example 1> Synthesis of Polyvalent Cyclic Carbodiimide (cc1)

cc1: Mw=516

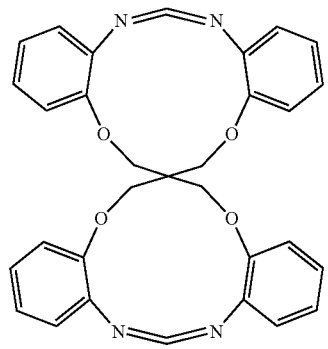 [SMILES: C1=Nc2ccccc2OCC2(COc3ccccc3N=1)COc1ccccc1N=C=Nc1ccccc1OC2]

Triphenylphosphine dibromide (0.11 mol) and 150 ml of 1,2-dichloroethane were fed to a reactor equipped with a stirrer, a heater and a dropping funnel in an N$_2$ atmosphere and stirred. A solution prepared by dissolving b1 (0.025 mol) synthesized in Production Example 1 and triethylamine (0.25 mol) in 50 ml of 1,2-dichloroethane was added dropwise to the resulting solution gently at 25° C. After the end of addition, a reaction was carried out at 70° C. for 5 hours. Thereafter, the reaction solution was filtered, and the filtrate was separated five times with 100 ml of water. An organic layer was dehydrated with 5 g of sodium sulfate, and 1,2-dichloroethane was removed under reduced pressure to obtain an intermediate product ca1 (triphenylphosphine compound).
Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an N$_2$ atmosphere and stirred. A solution prepared by dissolving the intermediate product ca1 (0.025 mol) in 100 ml of dichloromethane was added dropwise to the resulting solution gently at 25° C. After the end of addition, a reaction was carried out for 12 hours. Thereafter, a solid material obtained by removing dichloromethane was purified to obtain cc1. The structure of cc1 was checked by NMR and IR.
d1: 3,3'-diaminodiphenyl sulfone of Wako Pure Chemical Industries, Ltd.

d2: 4,4'-diaminodiphenyl sulfone of Wako Pure Chemical Industries, Ltd.

The above compounds and resins were each independently dried under reduced pressure at 25° C. for 5 hours before use.

Example 19

The numbers of parts by weight shown in Table 2 of a1 and b1 were mixed together, and the resulting mixture in a molten state was fed to a 30 ml-scale screw tubular bottle, heated until the inside temperature of the ON-300S constant-temperature drier (of AS One Corporation) became 80° C., taken out and stirred well with a stirrer. This operation was repeated three times to produce a homogeneous thermosetting resin composition.

1 g of this thermosetting resin composition was set on a Teflon (registered trademark)-coated stainless plate and cured at 200° C. for 2 hours by using the ON-300S constant-temperature drier (of AS One Corporation). Tg of the obtained cured resin is shown in Table 2. Even when the thermosetting resin composition was left at 10° C. for 60 minutes, it remained liquid and no viscosity change was observed.

Example 20

A cured resin was produced by curing at 200° C. for 4 hours in the same manner as in Example 19. Tg of the obtained cured resin is shown in Table 2.

Comparative Example 14

A cured resin was produced by curing at 200° C. for 2 hours in the same manner as in Example 19 except that b1 was changed to d1 and the number of parts by weight of d1 was set as shown in Table 2. Tg of the obtained cured resin is shown in Table 2.

Comparative Example 15

A cured resin was produced by curing at 200° C. for 4 hours in the same manner as in Comparative Example 14. Tg of the obtained cured resin is shown in Table 2.

Comparative Example 16

A cured resin was produced by curing at 200° C. for 2 hours in the same manner as in Example 19 except that b1 was changed to d2 and the number of parts by weight of d2 was set as shown in Table 2. Tg of the obtained sample is shown in Table 2.

Comparative Example 17

A cured resin was produced by curing at 200° C. for 4 hours in the same manner as in Comparative Example 16. Tg of the obtained cured resin is shown in Table 2.

Example 21

A cured resin was produced by curing at 180° C. for 2 hours in the same manner as in Example 14. Tg of the obtained cured resin is shown in Table 2.

Example 22

A cured resin was produced by curing at 180° C. for 4 hours in the same manner as in Example 19. Tg of the obtained cured resin is shown in Table 2.

Comparative Example 18

A cured resin was produced by curing at 180° C. for 2 hours in the same manner as in Comparative Example 14. Tg of the obtained cured resin is shown in Table 2.

Comparative Example 19

A cured resin was produced by curing at 180° C. for 4 hours in the same manner as in Comparative Example 14. Tg of the obtained cured resin is shown in Table 2.

Comparative Example 20

A cured resin was produced by curing at 180° C. for 2 hours in the same manner as in Comparative Example 16. Tg of the obtained cured resin is shown in Table 2.

Comparative Example 21

A cured resin was produced by curing at 180° C. for 4 hours in the same manner as in Comparative Example 16. Tg of the obtained cured resin is shown in Table 2.

Example 23

A cured resin was produced by curing at 160° C. for 2 hours in the same manner as in Example 19. Tg of the obtained cured resin is shown in Table 2.

Example 24

A cured resin was produced by curing at 160° C. for 4 hours in the same manner as in Example 19. Tg of the obtained cured resin is shown in Table 2.

Comparative Example 22

A cured resin was produced by curing at 160° C. for 2 hours in the same manner as in Comparative Example 14. Tg of the obtained cured resin is shown in Table 2.

Comparative Example 23

A cured resin was produced by curing at 160° C. for 4 hours in the same manner as in Comparative Example 14. Tg of the obtained cured resin is shown in Table 2.

Comparative Example 24

A cured resin was produced by curing at 160° C. for 2 hours in the same manner as in Comparative Example 16. Tg of the obtained cured resin is shown in Table 2.

Comparative Example 25

A cured resin was produced by curing at 160° C. for 4 hours in the same manner as in Comparative Example 16. Tg of the obtained cured resin is shown in Table 2.

Example 25

The numbers of parts by weight shown in Table 2 of a1, b1 and cc1 were mixed together, and the resulting mixture in a slurry state was fed to a 30 ml-scale screw tubular bottle, heated until the inside temperature of the ON-300S constant-temperature drier (of AS One Corporation) became 80° C., taken out and stirred well with a stirrer. This operation was repeated three times to produce a homogeneous thermosetting resin composition.

1 g of this thermosetting resin composition was set on a Teflon (registered trademark)-coated stainless plate and cured at 180° C. for 2 hours by using the ON-300S constant-temperature drier (of AS One Corporation). Tg of the obtained cured resin is shown in Table 2.

Example 26

A cured resin was produced by curing at 180° C. for 4 hours in the same manner as in Example 25. Tg of the obtained cured resin is shown in Table 2.

TABLE 2

|  |  |  | Unit | Ex. 19 | Ex. 20 | C. Ex. 14 | C. Ex. 15 | C. Ex. 16 | C. Ex. 17 | Ex. 21 | Ex. 22 |
|---|---|---|---|---|---|---|---|---|---|---|---|
| Thermosetting resin composition | Epoxy resin | a1 | parts by weight | 100 | 100 | 100 | 100 | 100 | 100 | 100 | 100 |
|  | Polyvalent amine-based curing agent | b1 | parts by weight | 35.3 | 35.3 | — | — | — | — | 35.3 | 35.3 |
|  | Other curing agent | cc1 | parts by weight | — | — | — | — | — | — | — | — |
|  |  | d1 | parts by weight | — | — | 34.9 | 34.9 | — | — | — | — |
|  |  | d2 | parts by weight | — | — | — | — | 34.9 | 34.9 | — | — |
| Cured resin | Curing temperature |  | ° C. | 200 | 200 | 200 | 200 | 200 | 200 | 180 | 180 |
|  | Curing time |  | Hour | 2 | 4 | 2 | 4 | 2 | 4 | 2 | 4 |
|  | Glass transition temperature (Tg) |  | ° C. | 189.5 | 194.5 | 173.2 | 176.9 | 190.4 | 211.6 | 188.8 | 194.8 |
|  | Tg difference (4 hours of curing − 2 hours of curing) |  | ° C. |  | 5 |  | 3.7 |  | 21.2 |  | 6 |

|  |  |  | Unit | C. Ex. 18 | C. Ex. 19 | C. Ex. 20 | C. Ex. 21 | Ex. 23 | Ex. 24 |
|---|---|---|---|---|---|---|---|---|---|
| Thermosetting resin composition | Epoxy resin | a1 | parts by weight | 100 | 100 | 100 | 100 | 100 | 100 |
|  | Polyvalent amine-based curing agent | b1 | parts by weight | — | — | — | — | 35.3 | 35.3 |
|  | Other curing agent | cc1 | parts by weight | — | — | — | — | — | — |
|  |  | d1 | parts by weight | 34.9 | 34.9 | — | — | — | — |
|  |  | d2 | parts by weight | — | — | 34.9 | 34.9 | — | — |
| Cured resin | Curing temperature |  | ° C. | 180 | 180 | 180 | 180 | 160 | 160 |
|  | Curing time |  | Hour | 2 | 4 | 2 | 4 | 2 | 4 |
|  | Glass transition temperature (Tg) |  | ° C. | 167.2 | 172.3 | 172.5 | 195.8 | 177.7 | 184.3 |
|  | Tg difference (4 hours of curing − 2 hours of curing) |  | ° C. |  | 5.1 |  | 23.3 |  | 6.6 |

|  |  |  | Unit | C. Ex. 22 | C. Ex. 23 | C. Ex. 24 | C. Ex. 25 | Ex. 25 | Ex. 26 |
|---|---|---|---|---|---|---|---|---|---|
| Thermosetting resin composition | Epoxy resin | a1 | parts by weight | 100 | 100 | 100 | 100 | 100 | 100 |
|  | Polyvalent amine-based curing agent | b1 | parts by weight | — | — | — | — | 35.3 | 35.3 |
|  | Other curing agent | cc1 | parts by weight | — | — | — | — | 5 | 5 |
|  |  | d1 | parts by weight | 34.9 | 34.9 | — | — | — | — |

TABLE 2-continued

|  |  |  | d2 | parts by weight | — | — | 34.9 | 34.9 | — | — |
|---|---|---|---|---|---|---|---|---|---|---|
| Cured resin | Curing temperature | ° C. |  |  | 160 | 160 | 160 | 160 | 180 | 180 |
|  | Curing time | Hour |  |  | 2 | 4 | 2 | 4 | 2 | 4 |
|  | Glass transition temperature (Tg) | ° C. |  |  | 156.9 | 168.4 | 141.6 | 172.3 | 196.4 | 198.7 |
|  | Tg difference (4 hours of curing − 2 hours of curing) | ° C. |  |  | 11.5 | | 30.7 | | 2.3 | |

Ex.: Example
C. Ex.: Comparative Example

It is understood from the above results that the thermosetting resin composition of the present invention achieves high Tg in a short curing time when the polyvalent amine-based curing agent (component b) represented by the formula (b-i) is used. It is also understood that, as compared with other curing agents, high Tg is achieved with this curing agent in a short curing time even at a low temperature. It is further understood that handling is excellent as this effect is promoted by heating without curing right after the components are mixed together. The effect can be further enhanced by using the cyclic carbodiimide compound (component B) as the other curing agent.

Effect of the Invention

The thermosetting resin composition comprising the cyclic carbodiimide compound (component B) of the present invention provides a cured resin having high heat resistance without producing a free isocyanate compound during a high-temperature treatment. Further, since the carbodiimide compound is used, reactivity at a low temperature can be controlled and flowability at the time of processing can be retained. In addition, adhesion to another member can be kept high due to the existence of the carbodiimide compound and a reaction product thereof.

It is assumed that the cyclic carbodiimide compound (component B) remains as an isocyanate group (—NCO) at the end of the epoxy resin after its reaction and this isocyanate group further contributes to the reaction, thereby raising the glass transition temperature of the cured resin.

It was confirmed from this study that a thermosetting resin composition prepared by adding a carbodiimide compound having a specific cyclic structure to a specific epoxy resin and a curing agent has an improved curing speed. Therefore, the thermosetting resin composition of the present invention can be advantageously used as a semiconductor sealing material or a carbon fiber composite material in fields in which high heat resistance is required, such as electric and electronic devices, automobiles and aircrafts.

The thermosetting resin composition comprising the polyvalent amine-based compound (component b) represented by the formula (b-i) of the present invention makes it possible to reduce the curing temperature at the time of thermal curing and to shorten the thermal curing time due to the polyvalent amine-based compound (component b). Further, a cured resin having a high glass transition temperature can be obtained after curing. Therefore, the thermosetting resin composition of the present invention can be advantageously used as a semiconductor sealing material or a carbon fiber composite material in fields in which high heat resistance is required, such as electric and electronic devices and automobiles and aircrafts, and the obtained cured resin is useful in the above applications.

The thermosetting resin composition comprising the cyclic carbodiimide compound (component B) and the polyvalent amine-based compound (component b) represented by (b-i) of the present invention can achieve high Tg in a short curing time. As compared with other curing agents, high Tg is achieved in a short curing time even at a low temperature. Further, the amount of a free isocyanate compound produced at the time of a high-temperature treatment is small, and adhesion and flowability at the time of processing are high.

INDUSTRIAL APPLICABILITY

The thermosetting resin composition of the present invention can be expected to have high heat resistance, high adhesion to another member and high flowability at the time of processing as it comprises a cyclic carbodiimide compound. The thermosetting resin composition can be advantageously used especially for applications in which high heat resistance is required, for example, semiconductor sealing materials, prepregs and other composite matrix materials, printed circuit boards, laminate sheets, electrical insulating materials and pastes. Since it does not cure drastically at the time of mixing, its handling is excellent.

The thermosetting resin composition comprising the polyvalent amine-based compound having a specific structure of the present invention has high heat resistance, fast curability at the time of heating and curing properties at a relatively low temperature, and a satisfactory pot life can be expected from the viewpoint of handling. The thermosetting resin composition of the present invention can be advantageously used especially for applications in which heat resistance is required, for example, semiconductor sealing materials, prepregs and other composite matrix materials, printed circuit boards, laminate sheets, electrical insulating materials and pastes.

What is claimed is:

1. A thermosetting resin composition comprising:
   (A) an epoxy resin (component A);
   (B) a cyclic carbodiimide compound (component B) including a cyclic structure having one carbodiimide group and represented by the following formula (B-i) in which first nitrogen and second nitrogen are bonded together by a bond group and having 8 to 50 atoms forming the cyclic structure:

(B-i)

wherein Q is bivalent to tetravalent bond group which is an aliphatic group, alicyclic group, aromatic group or a combination of these groups, and may contain a hetero atom or substituent; and (b) a polyvalent amine-based curing agent (component b) represented by the following formula (b-i):

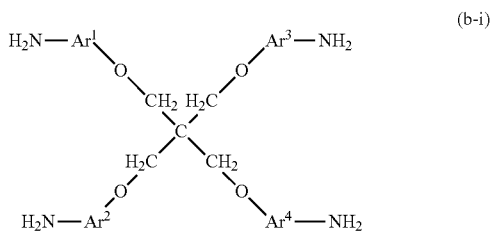

(b-i)

wherein $Ar^1$ to $Ar^4$ are each independently a phenylene group or naphthalene-diyl group which may be substituted by a substituent.

2. The thermosetting resin composition according to claim 1, wherein the component B is a polyvalent cyclic carbodiimide compound having at least two carbodiimide groups in one molecule.

3. The thermosetting resin composition according to claim 1, wherein the component B is a compound represented by the following formula (B-ii):

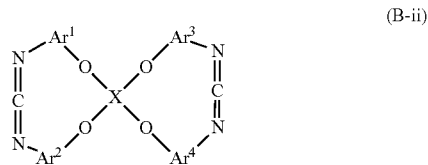

(B-ii)

wherein X is a tetravalent group represented by the following formula (B-iii); $Ar^1$ to $Ar^4$ are each independently an orthophenylene group or 1,2-naphthalene-diyl group which may be substituted by an alkyl group having 1 to 6 carbon atoms or phenyl group;

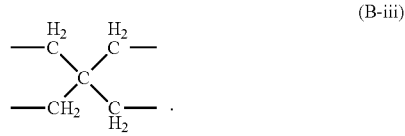

(B-iii)

4. The thermosetting resin composition according to claim 1, wherein the content of the cyclic carbodiimide compound (component B) is 0.01 to 50 parts by weight based on 100 parts by weight of the epoxy resin (component A).

5. The thermosetting resin composition according to claim 1, wherein the glass transition temperature of a cured resin is 2° C. or more higher than the glass transition temperature of a cured resin obtained by curing a thermosetting resin composition comprising no component B under the same conditions.

6. The thermosetting resin composition according to claim 1, further comprising a curing agent (component C).

7. The thermosetting resin composition according to claim 1, further comprising a curing accelerator (component D).

8. A thermosetting resin composition comprising:
(A) an epoxy resin (component A); and
(b) a polyvalent amine-based curing agent (component b) represented by the following formula (b-i):

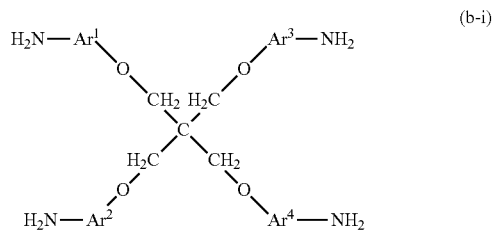

(b-i)

wherein $Ar^1$ to $Ar^4$ are each independently a phenylene group or naphthalene-diyl group which may be substituted by a substituent.

9. The thermosetting resin composition according to claim 8, comprising 10 to 50 parts by weight of the polyvalent amine-based curing agent (component b) based on 100 parts by weight of the epoxy resin (component A).

10. The thermosetting resin composition according to claim 8, comprising 10 to 45 parts by weight of the polyvalent amine-based curing agent (component b) based on 100 parts by weight of the epoxy resin (component A).

11. The thermosetting resin composition according to claim 8, wherein the difference between the glass transition temperature (Tg·2H) of a cured resin after 2 hours of curing and the glass transition temperature (Tg·4H) of a cured resin after 4 hours of curing is less than 10° C. at a thermal curing temperature of 160° C. to 200° C.

12. The thermosetting resin composition according to claim 8, wherein the glass transition temperature (Tg·160° C./4H) of a cured resin obtained after 4 hours of curing at a thermal curing temperature of 160° C. is 175° C. or higher.

13. The thermosetting resin composition according to claim 8, wherein the glass transition temperature (Tg·180° C./2H) of a cured resin obtained after 2 hours of curing at a thermal curing temperature of 180° C. is 175° C. or higher.

14. The thermosetting resin composition according to claim 8, wherein the epoxy resin (component A) is a bisphenol type epoxy resin.

* * * * *